(12) United States Patent
Karbowniczek et al.

(10) Patent No.: US 9,005,233 B2
(45) Date of Patent: Apr. 14, 2015

(54) CONTACT ACTIVATED LANCET DEVICE

(75) Inventors: Jarek Grzegorz Karbowniczek, Warsaw (PL); Wlodzinierz Rutynowski, Warsaw (PL); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 419 days.

(21) Appl. No.: 12/815,005

(22) Filed: Jun. 14, 2010

(65) Prior Publication Data
US 2010/0305599 A1 Dec. 2, 2010

Related U.S. Application Data

(62) Division of application No. 11/123,849, filed on May 6, 2005.

(60) Provisional application No. 60/569,424, filed on May 7, 2004, provisional application No. 60/631,846, filed on Nov. 30, 2004, provisional application No. 60/631,795, filed on Nov. 30, 2004, provisional application No. 60/669,276, filed on Apr. 7, 2005.

(51) Int. Cl.
*A61B 17/14* (2006.01)
*A61B 5/151* (2006.01)
*A61B 5/15* (2006.01)
*A61B 17/00* (2006.01)

(52) U.S. Cl.
CPC ........... *A61B 5/15142* (2013.01); *A61B 5/1411* (2013.01); *A61B 2017/00424* (2013.01)

(58) Field of Classification Search
USPC .......... 606/181–183, 185; 604/157, 134–138; D24/146, 147; 600/583
See application file for complete search history.

(56) References Cited

U.S. PATENT DOCUMENTS

| 3,741,197 A | 6/1973 | Sanz et al. |
| 4,388,925 A | 6/1983 | Burns |
| 4,442,836 A * | 4/1984 | Meinecke et al. ............ 606/182 |
| 4,527,561 A | 7/1985 | Burns |
| 4,577,630 A | 3/1986 | Nitzsche et al. |

(Continued)

FOREIGN PATENT DOCUMENTS

| CN | 1520893 A | 8/2004 |
| CN | 1525837 A | 9/2004 |

(Continued)

*Primary Examiner* — Elizabeth Houston
*Assistant Examiner* — Robert Lynch
(74) *Attorney, Agent, or Firm* — The Webb Law Firm

(57) ABSTRACT

A lancet device including a housing and a lancet structure having a puncturing element. The lancet structure disposed within the housing and adapted for movement between a retaining or pre-actuated position wherein the puncturing element is retained within the housing, and a puncturing position wherein the puncturing element extends through a forward end of the housing. The lancet device includes a drive spring disposed within the housing for biasing the lancet structure toward the puncturing position, and a retaining hub retaining the lancet structure in the retracted position against the bias of the drive spring. The retaining hub includes a pivotal lever in interference engagement with the lancet structure. An actuator within the housing pivots the lever, thereby moving the lancet structure toward the rearward end of the housing to at least partially compress the drive spring, and releasing the lever from interference engagement with the lancet structure.

60 Claims, 33 Drawing Sheets

(56) References Cited

U.S. PATENT DOCUMENTS

| | | | |
|---|---|---|---|
| 4,637,403 A * | 1/1987 | Garcia et al. ............ 600/583 |
| 4,653,513 A | 3/1987 | Dombrowski |
| 4,817,603 A | 4/1989 | Turner et al. |
| 4,869,249 A | 9/1989 | Crossman et al. |
| 4,924,879 A | 5/1990 | O'Brien |
| 4,994,068 A | 2/1991 | Hufnagle |
| 5,100,427 A | 3/1992 | Crossman et al. |
| 5,314,441 A | 5/1994 | Cusack et al. |
| 5,366,470 A | 11/1994 | Ramel |
| 5,439,473 A | 8/1995 | Jorgensen |
| 5,540,664 A | 7/1996 | Wyrick |
| 5,540,709 A | 7/1996 | Ramel |
| 5,554,166 A | 9/1996 | Lange et al. |
| 5,569,286 A | 10/1996 | Peckham et al. |
| 5,611,809 A | 3/1997 | Marshall et al. |
| 5,643,306 A | 7/1997 | Schraga |
| 5,707,384 A | 1/1998 | Kim |
| 5,755,733 A | 5/1998 | Morita |
| 5,908,434 A | 6/1999 | Schraga |
| 5,984,940 A | 11/1999 | Davis et al. |
| 6,053,930 A | 4/2000 | Ruppert |
| 6,066,103 A | 5/2000 | Duchon et al. |
| 6,168,606 B1 | 1/2001 | Levin et al. |
| 6,248,120 B1 | 6/2001 | Wyszogrodzki |
| 6,258,112 B1 | 7/2001 | Schraga |
| 6,299,626 B1 | 10/2001 | Viranyi |
| 6,322,574 B1 | 11/2001 | Lloyd et al. |
| 6,432,120 B1 | 8/2002 | Teo |
| 6,514,270 B1 | 2/2003 | Schraga |
| D499,182 S | 11/2004 | Moore et al. |
| 6,852,119 B1 | 2/2005 | Abulhaj et al. |
| 2002/0128608 A1 | 9/2002 | Teo et al. |
| 2004/0133172 A1 | 7/2004 | Wilkinson |
| 2006/0052809 A1 | 3/2006 | Karbowniczek et al. |

FOREIGN PATENT DOCUMENTS

| | | |
|---|---|---|
| EP | 0569124 A1 | 11/1993 |
| EP | 0582226 B1 | 10/1997 |
| EP | 1247489 A1 | 10/2002 |
| JP | 57-168644 A | 10/1982 |
| JP | 61286738 A | 12/1986 |
| JP | 6238140 A | 2/1987 |
| JP | 67329 A | 1/1994 |
| JP | 07-500995 A | 2/1995 |
| JP | 2001-078991 A | 3/2001 |
| JP | 2001-353138 A | 12/2001 |
| JP | 2003-325484 A | 11/2003 |
| JP | 2003-339679 A | 12/2003 |
| JP | 2005-518858 A | 6/2005 |
| JP | 2006-504502 A | 2/2006 |
| WO | 03049613 A1 | 6/2003 |
| WO | 03/073936 A2 | 9/2003 |
| WO | 03092512 A1 | 11/2003 |
| WO | 2004/039429 A2 | 5/2004 |
| WO | 2005034753 A1 | 4/2005 |

* cited by examiner

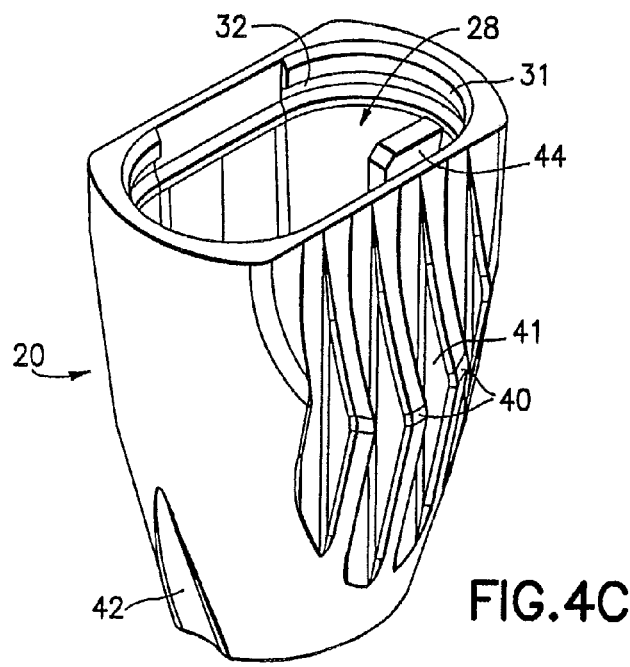
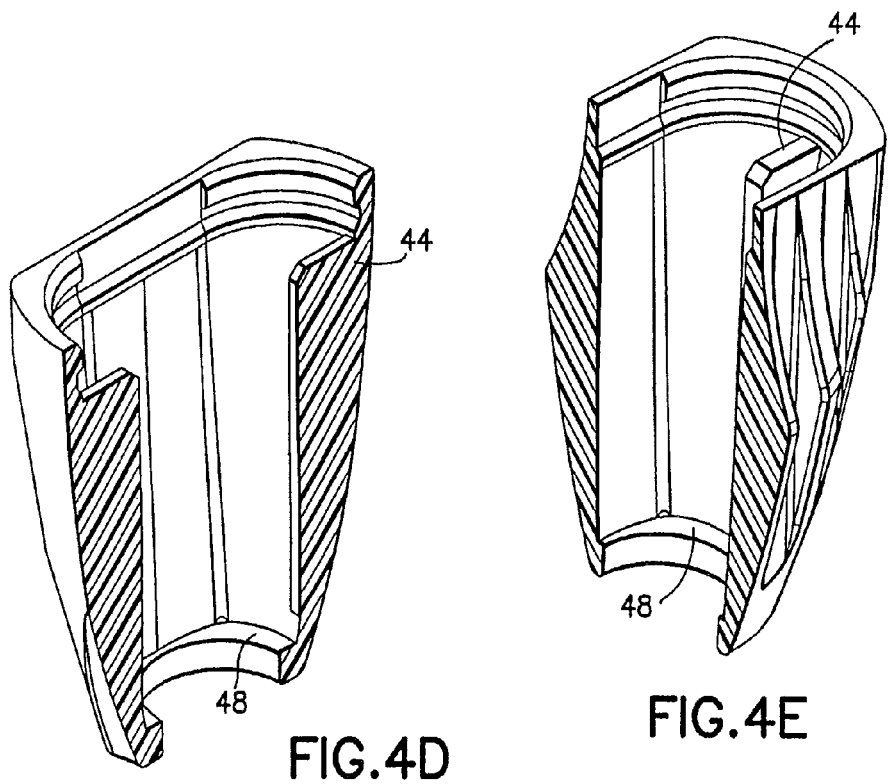

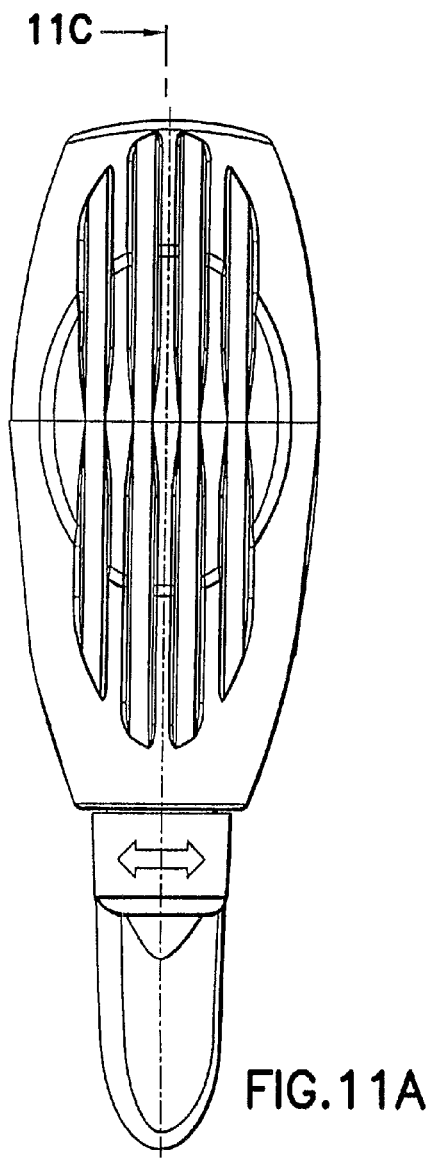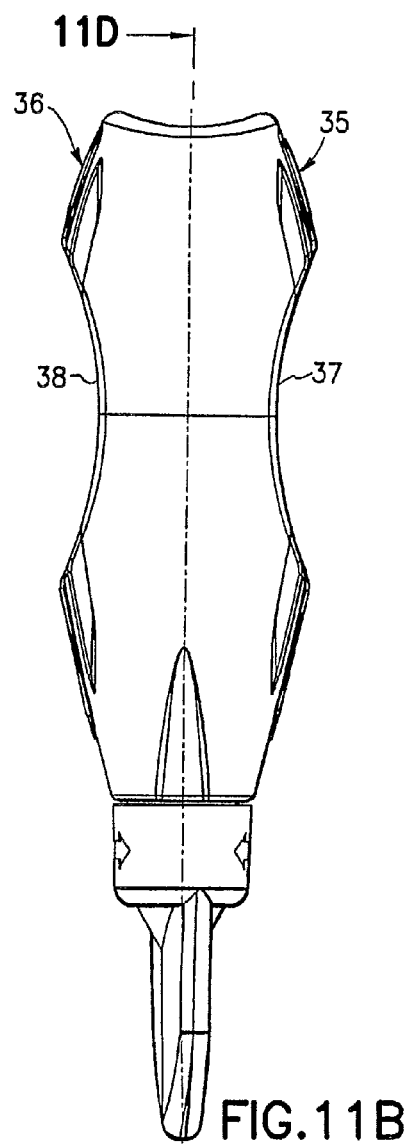
FIG.11A
FIG.11B

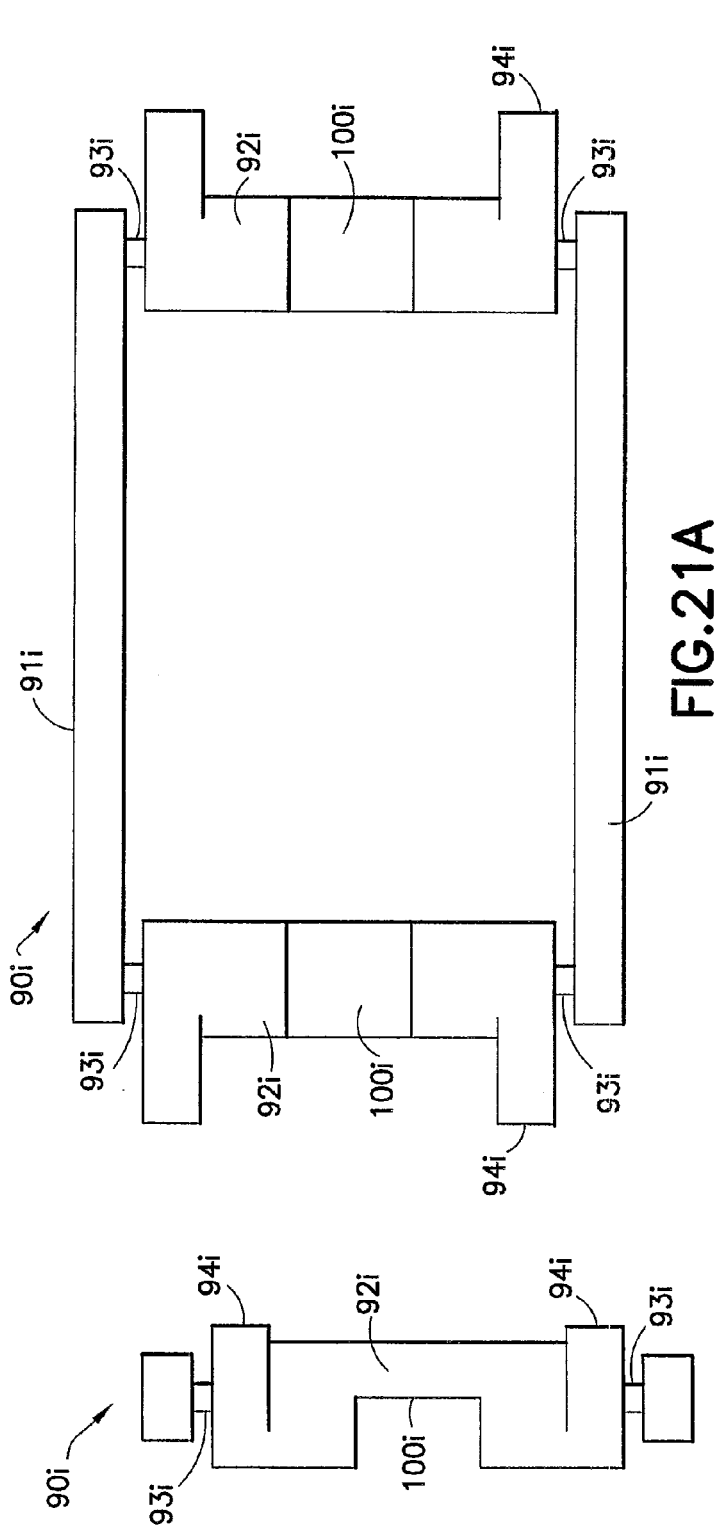
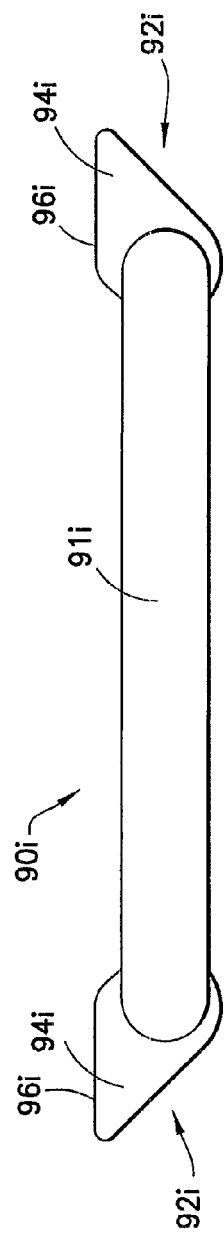
FIG.21A
FIG.21B
FIG.21C

CONTACT ACTIVATED LANCET DEVICE

CROSS REFERENCE TO RELATED APPLICATIONS

The present application claims priority to U.S. application Ser. No. 11/123,849 filed May 6, 2005 entitled "Contact Activated Lancet Device", U.S. Application No. 60/569,424 filed May 7, 2004, U.S. Application No. 60/631,846 filed Nov. 30, 2004, U.S. Application No. 60/631,795 filed Nov. 30, 2004, and U.S. Application No. 60/669,276 filed Apr. 7, 2005.

BACKGROUND OF THE INVENTION

1. Field of the Invention

The present invention relates generally to medical puncturing devices, commonly referred to as lancets, which are used to take blood samples from patients and, more specifically, to a lancet device that is designed for ease of use with activation achieved during contact of the device in normal use.

2. Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design involves preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Examples of such medical puncturing devices are disclosed in U.S. Pat. Nos. 6,432,120; 6,248,120; 5,755,733; and 5,540,709.

U.S. Pat. No. 6,432,120 to Teo discloses a lancet device that includes a lancet holder which contains a spring-loaded lancet structure. The spring-loaded lancet structure includes a single spring that effects the ejection and retraction of a lancet needle upon the triggering of the structure. U.S. Pat. No. 6,248,120 to Wyszogrodzki discloses a lancet device comprised of a housing, a shielding portion, a piston with a puncturing tip, and drive and return springs that eject and retract the piston, respectively, upon the breakage of internal wing elements in the housing. U.S. Pat. No. 5,755,733 to Morita discloses a lancet device that includes a combined holder and lancet structure. The lancet structure includes a lancet member with a puncturing tip and a compressible spring member that causes the lancet member to puncture the skin of a patient upon actuation of a pair of actuating arms.

U.S. Pat. No. 5,540,709 to Ramel discloses a lancet device that includes a housing enclosing a slidable trigger, which is used to trigger a compressed spring that powers a piercing lancet member to pierce the skin of a patient. The housing includes a pair of internal fingers that engage and hold the body of the lancet member, which are then released of engagement with the lancet member body by axial force applied by the user to the slidable trigger. Other medical puncturing devices or lancets known in the art are disclosed in U.S. Pat. Nos. 4,869,249 and 4,817,603. The devices disclosed in these references include a cap that is used to protect a needle or to keep the needle sterile.

SUMMARY OF THE INVENTION

In view of the foregoing, a need generally exists in the medical field for a medical puncturing device that is easy for a user to manipulate and use while ensuring sterility before use and safe and secure disposal after use. Additionally, a need exists in the medical field for a simple, reliable, self-activating, and disposable medical puncturing device for use in collecting blood samples.

A lancet device in an embodiment of the invention generally includes a housing and a lancet structure having a puncturing element, with the lancet structure disposed within the housing and adapted for movement between a retaining or pre-actuated position wherein the puncturing element is retained within the housing, and a puncturing position wherein the puncturing element extends through a forward end of the housing. The lancet device further includes a drive spring for biasing the lancet structure toward the puncturing position. The drive spring may be disposed between a rearward end of the housing and the lancet structure, and may be a separate structure or may be integrally formed with one or both of the housing and/or the lancet structure. The lancet device further includes a lever element pivotal about a fulcrum providing interference engagement with the lancet structure and retaining the lancet structure in the retracted position against the bias of the drive spring. The lever element may include a retaining hub including a pivotal lever in interference engagement with the lancet structure and pivotal about a fulcrum of the retaining hub. Movement of the housing and the retaining hub with respect to each other, such as axial or longitudinal movement, causes the lever to pivot about a fulcrum, thereby releasing the lever from interference engagement with the lancet structure and, typically, moving the lancet structure toward the rearward end of the housing to at least partially compress the drive spring. With the lancet structure released from the lever, the drive spring drives the lancet structure through the housing toward the puncturing position.

The lever may include a shoulder in interference engagement with the lancet structure and a contact surface for engagement with an internal contact within the housing. The housing may include an internal contact therein for pivoting of the lever, which may be an integrally formed cam surface for cooperating engagement with the contact surface of the lever. The lever may be a class 1 type lever, with a pivoting point or fulcrum between the load element and the force element, such as a see-saw type of lever. Desirably, the lever is a wedge pivotally hinged to the retaining hub forming a pivot hinge defining the fulcrum for cooperative pivoting of the shoulder and the contact surface about the hinge or fulcrum. Moreover, the retaining hub may include an annular rim, with the lever pivotally hinged to the annular rim.

In a further embodiment of the invention, a lancet device includes a housing and a lancet structure adapted for axial or longitudinal movement through the housing between a pre-actuated position with a puncturing element of the lancet structure retained within the housing and a puncturing position with the puncturing element extending through a forward end of the housing. A drive spring biases the lancet structure toward the puncturing position, and a retaining hub retains the lancet structure in the pre-actuated position against the bias of the drive spring. The retaining hub includes a lever pivotal about a fulcrum, with the lever in interference engagement with the lancet structure. An actuator is adapted to pivot the lever about the fulcrum to release the lever from interference engagement with the lancet structure, thereby permitting the drive spring to drive the lancet structure to the puncturing position.

The actuator may include an actuator element extending through and into the housing, such as a push button element extending through a rearward end of the housing which is axially movable with respect to the housing to cause the actuator element to pivot the lever about the fulcrum. Alternatively, the actuator may include an internal contact within the housing such as an internal contact integrally formed within the housing, such that axial movement of the housing toward the retaining hub causes the internal contact within the housing to pivot the lever about the fulcrum.

Desirably, the lancet device further includes a shield extending through the forward end of the housing and axially or longitudinally movable with respect to the housing, with the retaining hub adjacent the rearward end of the shield. The lancet structure may be retained by the retaining hub at the rearward end of the shield. In this manner, relative axial or longitudinal movement of the rearward end of the shield and the rearward end of the housing toward each other causes the internal contact within the housing to pivot the lever of the retaining hub, thereby actuating the device by releasing the interference engagement between the lever and the lancet structure. Desirably, the lancet structure and the shield include corresponding guiding surfaces for guiding the lancet structure axially or longitudinally through the shield.

In a further embodiment, a lancet device includes a housing having a rearward end and a forward end having an opening extending therethrough, and a shield movable through the opening of the forward end of the housing, such as axially or longitudinally, with the shield including a lever element, such as a retaining hub adjacent a rearward end thereof, including a pivotal lever. A lancet structure with a puncturing element is disposed within the housing. The lancet structure is in interference engagement with the lever of the retaining hub at the rearward end of the shield, and is adapted for axial or longitudinal movement between a retaining or pre-actuated position with the puncturing element disposed within the housing, and a puncturing position with the puncturing element extending through a forward end of the shield. A drive spring is disposed between the housing and the lancet structure for biasing the lancet structure against the lever of the retaining hub, with the interference engagement between the lever and the lancet structure maintaining the lancet structure in the retaining or pre-actuated position. Axial or longitudinal movement of the shield toward the rearward end of the housing causes an internal contact within the housing to engage the lever of the retaining hub, thereby causing pivotal movement of the lever to release the interference engagement between the lever and the lancet structure. The drive spring may thereafter drive the lancet structure axially or longitudinally through the shield toward the puncturing position.

The retaining hub desirably includes an annular rim, which may be separate from and retained within the rearward end of the shield, with at least one lever pivotally supported on the annular rim. More desirably, a pair of levers are pivotally supported on opposing sides of the annular rim. The lever may further include a shoulder for interference engagement with the lancet structure, as well as a contact surface for engagement with the internal contact of the housing to cause the lever to pivot, thereby releasing the lancet structure from interference engagement with the shoulder. For example, the internal contact of the housing may include an integrally formed cam surface for cooperating engagement with the contact surface of the lever. The lever may be in the form of a wedge pivotally hinged to the retaining hub forming a pivot hinge for cooperative pivoting of the shoulder and the contact surface.

The lancet device may further include a retraction spring for retracting the lancet structure within the shield after the drive spring drives the lancet structure axially through the shield toward the puncturing position. For example, the retraction spring may be a compression spring positioned within the forward end of the shield for compression between the lancet structure and the forward end of the shield. The biasing force of the compression spring between the forward end of the shield and the lancet structure should exceed the biasing force of the drive spring between the rearward end of the housing and the lancet structure after the drive spring drives the lancet device to the puncturing position. In this manner, the retraction spring may retract the lancet structure within the shield and/or the housing, thereby maintaining the puncturing element therein. The shield and housing may further include locking structure extending therebetween for maintaining the shield in fixed relation to the housing after the drive spring drives the lancet structure through the shield toward the puncturing position.

In yet a further embodiment, an improved lancet device includes a housing and a lancet axially or longitudinally movable within the housing and retained within the housing against a bias of a drive spring which biases the lancet toward a puncturing position in which a puncturing element extends through a forward end of the housing. The improved lancet device includes a retaining hub, such as an annular structure, having at least one lever in interference engagement with the lancet for retaining the lancet within the housing against the bias of the drive spring, with the lever being pivotal about a fulcrum. Pivoting of the lever about the fulcrum releases the lancet from interference engagement with the lever to permit the drive spring to drive the lancet axially or longitudinally toward the puncturing position. The lever and fulcrum may be provided on one side of a plane dissecting the retaining hub at a cross section to an axis defined by the lancet.

In one variation of this embodiment, axial or longitudinal movement of the housing and the retaining hub with respect to each other causes an internal contact within the housing to pivot the lever about the fulcrum. This may be accomplished through a shield extending through a forward end of the housing and axially or longitudinally moveable with respect to the housing, with the retaining hub adjacent a rearward end of the shield. At least a portion of the lancet is axially or longitudinally moveable through the shield and the retaining hub upon release of the lancet from interference engagement with the lever. In a further variation, an actuator having an actuation element extends through and into the housing, desirably through the rearward end of the housing. Movement of the actuation element with respect to the housing causes the actuation element to pivot the lever about the fulcrum. In yet a further variation, the retaining hub may be unitary with the shield, and may be an annular structure.

A further embodiment provides an improved method of retaining a lancet structure in a pre-actuated position within a housing against the bias of a drive spring by providing a retaining hub in the form of an annular rim including a lever in interference engagement with the lancet structure. The lever is pivotal about a fulcrum, such that pivoting of the lever about the fulcrum releases the interference engagement between the lever and the lancet structure, permitting the drive spring to drive the lancet structure toward a puncturing position with a puncturing element extending through a forward end of the housing.

Yet a further embodiment provides a method of actuating a lancet device. The method includes providing a lancet device comprising a housing, a lancet structure disposed within the housing and including a puncturing element retained within the housing, a drive spring biased against the lancet structure, such as between a rearward end of the housing and the lancet structure, and a retaining hub retaining the lancet structure within the housing against the bias of the drive spring through a pivotal lever in interference engagement with the lancet structure. To actuate the device, the lever is contacted with an actuator to pivot the lever, thereby sequentially causing the lancet structure to move toward the rearward end of the housing to compress the drive spring and releasing the interference engagement between the lever and the lancet structure. This release causes the drive spring to drive the lancet structure axially toward a puncturing position wherein the puncturing element extends through a forward end of the housing. Other embodiments where the drive spring is constrained from further compression are also contemplated. For example, the drive spring may reach its solid height and not permit further compression while still allowing movement of the retaining hub with respect to the housing as well as release of interference engagement between the lever and the lancet structure.

The actuator desirably includes an internal contact within the housing, with the contacting step involving axially or longitudinally displacing the housing and the retaining hub toward each other to cause the internal contact of the housing to pivot the lever. Moreover, the lancet device may further include a shield extending through the forward end of the housing and axially movable with respect to the housing, with the retaining hub adjacent the rearward end of the shield for retaining the lancet structure within the housing against the bias of the drive spring. In such an embodiment, the method further includes a displacement step involving axially or longitudinally displacing the rearward end of the shield and the rearward end of the housing relative to each other to cause the contacting step. For example, the displacement step may involve applying external pressure between a forward end of the shield and the rearward end of the housing. Also, the lever may include a shoulder in interference engagement with the lancet structure and a contact surface for engagement with the internal contact of the housing. In this manner, the contacting step involves engaging the internal contact of the housing with the contact surface of the lever to pivot the lever.

Further, the retaining hub may include an annular rim with the lever pivotally hinged to the annular rim such that the shoulder extends radially inward of the annular rim and the contact surface is at an external perimeter of the annular rim. In this manner, the contacting step involves engaging the internal contact of the housing with the contact surface of the lever at an external perimeter of the annular rim, thereby pivoting the lever by tipping the contact surface and the shoulder to release the lancet structure through the annular rim and through the shield.

The method may involve a further step of retracting the puncturing element within the housing after the puncturing element reaches the puncturing position. In particular, the lancet device may further include a compression spring positioned within the forward end of the shield. The retraction step involves compressing the compression spring between the lancet structure and the forward end of the shield through the bias of the drive spring and thereafter relaxing the compression spring. In an embodiment of the invention, the biasing force of the compression spring between the forward end of the shield and the lancet structure in a relaxed state exceeds the biasing force of the drive spring between the rearward end of the housing and the lancet structure after the drive spring drives the lancet device to the puncturing position. Accordingly, the puncturing element is retracted within the shield, thereby maintaining the lancet structure within the housing.

Further details and advantages will become apparent from the following detailed description when read in conjunction with the accompanying drawings.

BRIEF DESCRIPTION OF THE DRAWINGS

FIGS. 4B and 4C are top perspective views of the main body of the housing of FIG. 4A.

FIGS. 4D and 4E are opposing sectional views of the main body as shown in FIG. 4C.

FIGS. 11A and 11B are front and side perspective views of the lancet device of FIG. 1.

FIGS. 21A-21C are bottom, side, and end views, respectively, of a retaining hub used in the lancet device shown in FIG. 53.

DESCRIPTION OF THE PREFERRED EMBODIMENTS

Figure 1:
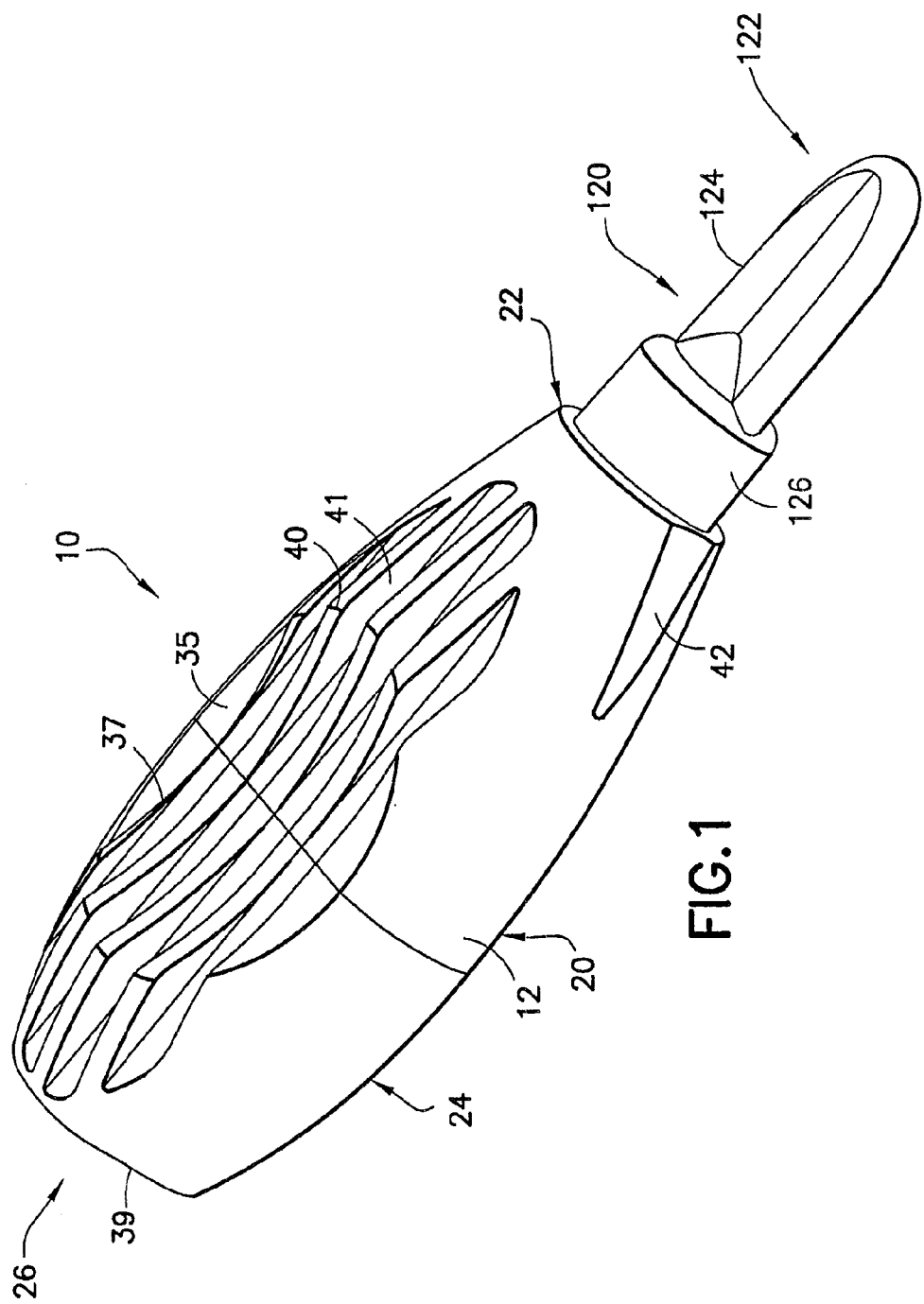
FIG. 1 is perspective view of a lancet device in accordance with an embodiment of the present invention.

For purposes of the description hereinafter, the words "upper", "lower", "right", "left", "vertical", "horizontal", "top", "bottom", "lateral", "longitudinal", "axial", and like terms, if used, shall relate to the invention, as it is oriented in the drawing figures. Additionally, the term "distal" shall refer to the portion of the device closest the puncture end and the term "proximal" shall refer to the portion of the device opposite the distal portion. It is to be understood that the invention may assume many alternative variations and embodiments except where expressly specified to the contrary. It is also to be understood that the specific devices and embodiments illustrated in the accompanying drawings and described herein are simply exemplary embodiments of the invention.

Figure 2:
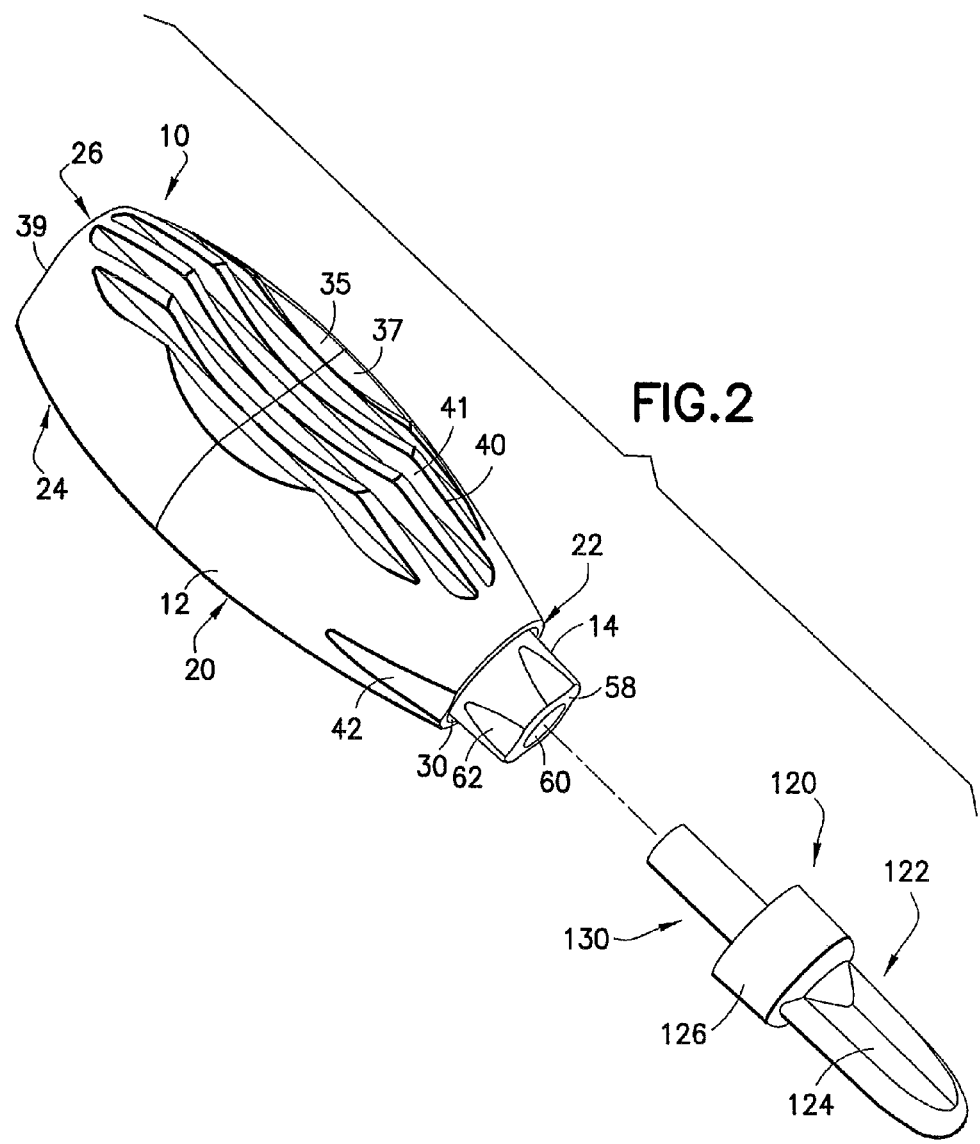
FIG. 2 is perspective view of the lancet device of FIG. 1 showing the protective cover separated from the body of the lancet device.
Figure 3:
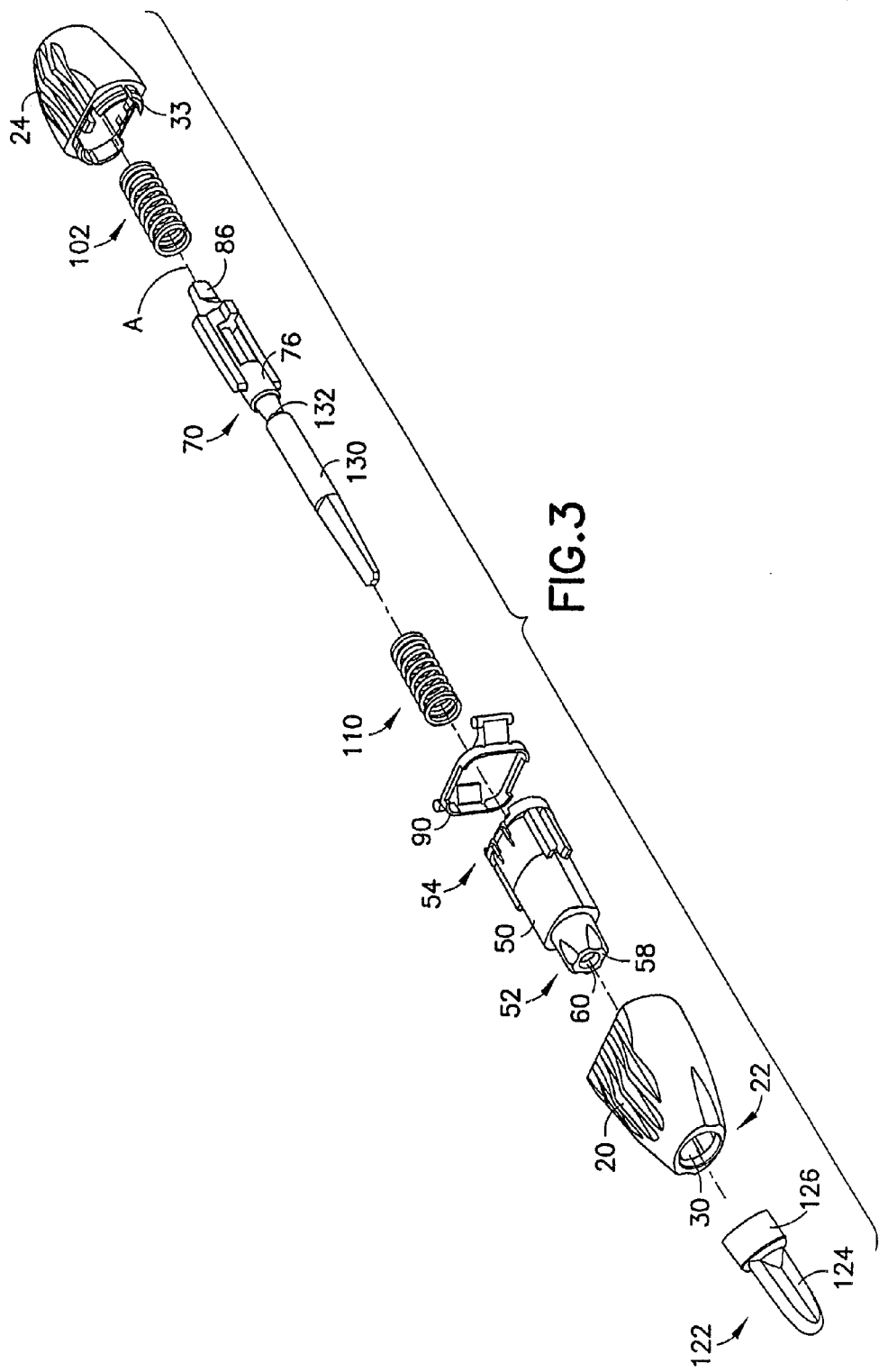
FIG. 3 is an exploded perspective view of the lancet device of FIG. 1.
Figure 4A:
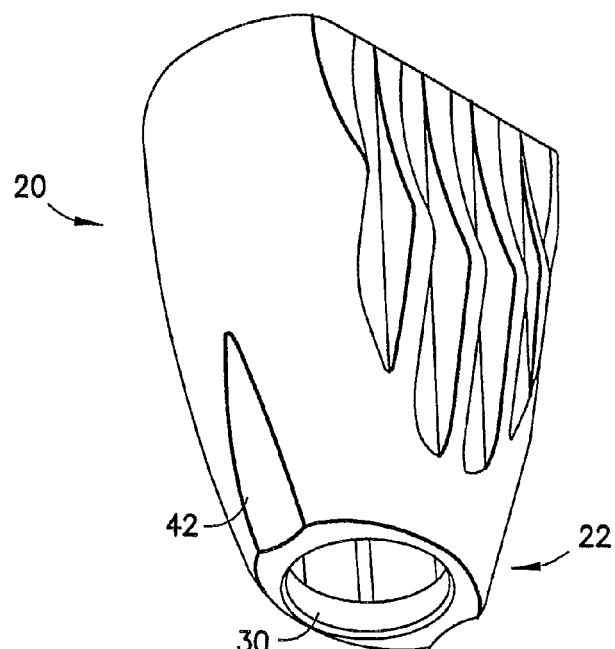
FIG. 4A is a bottom perspective view of the main body of the housing in an embodiment of the present invention.
Figure 4B:
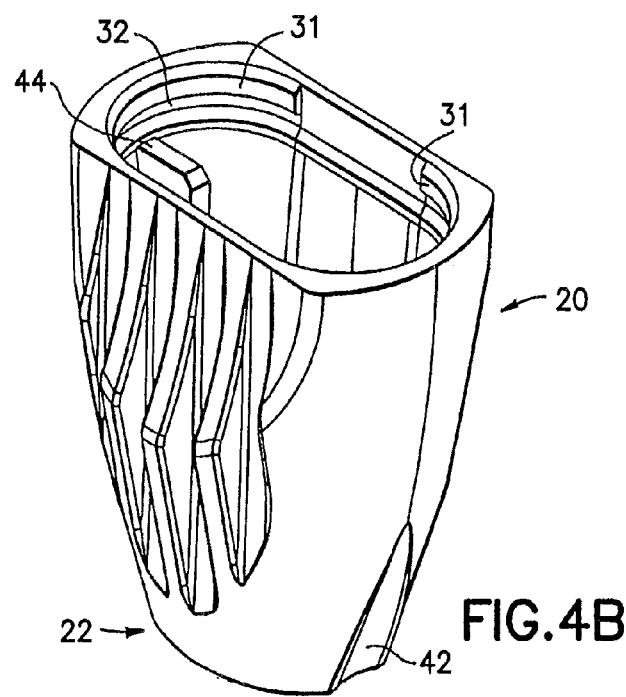
Figure 5A:
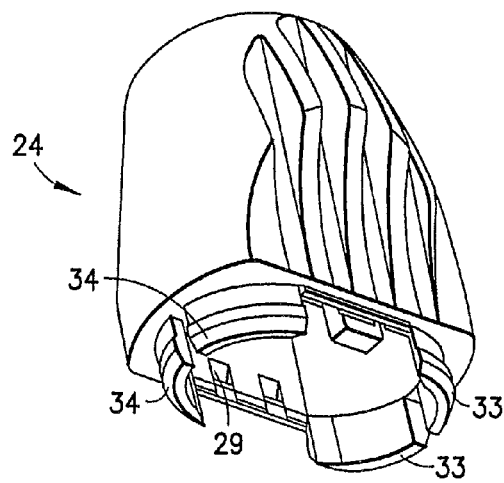
FIG. 5A is a bottom perspective view of the rear cap of the housing in an embodiment of the present invention.
Figure 5B:
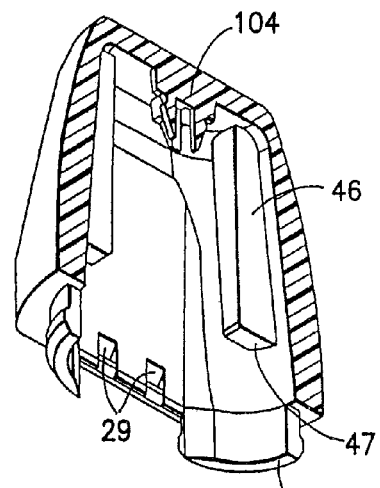
FIGS. 5B and 5C are opposing sectional views of the rear cap as shown in FIG. 5A.
Figure 5C:
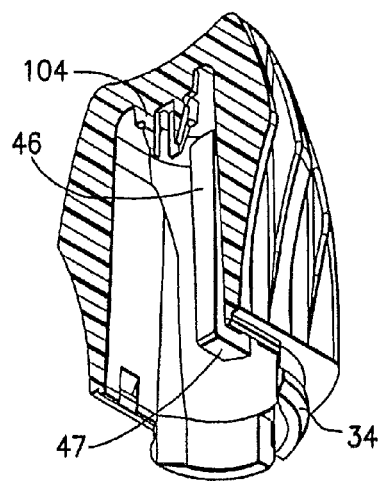
Figure 5D:
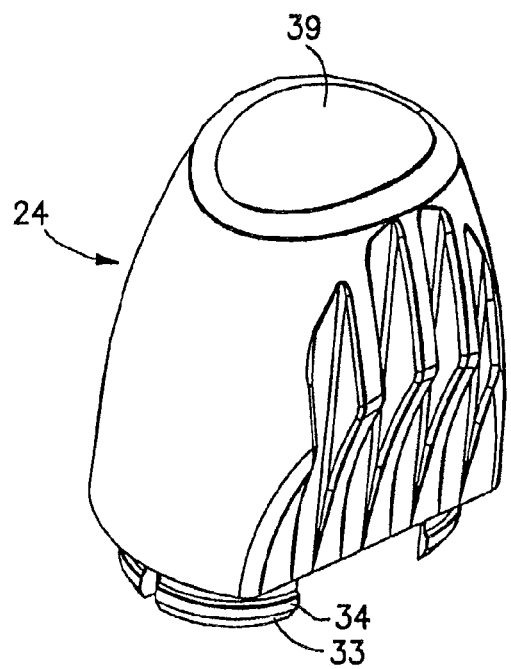
FIG. 5D is a top perspective view of the rear cap of the housing of FIG. 5A.
Figure 5E:
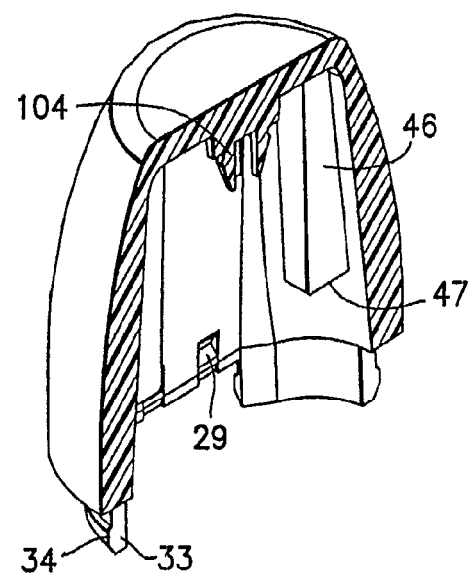
FIG. 5E is a sectional view of the rear cap as shown in FIG. 5D.
Figure 6A:
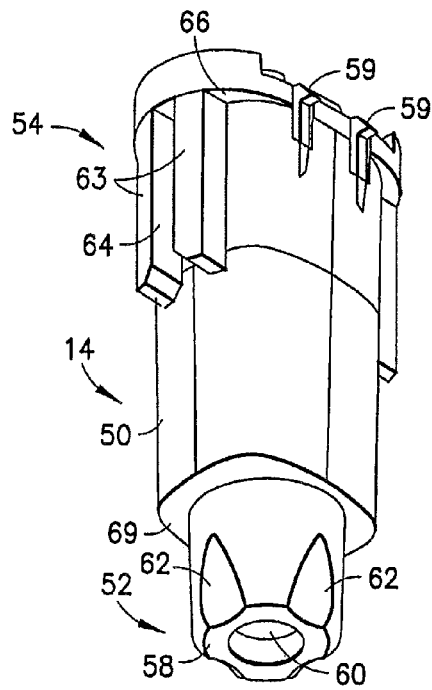
FIG. 6A is a bottom perspective view of the shield in an embodiment of the present invention.
Figure 6B:
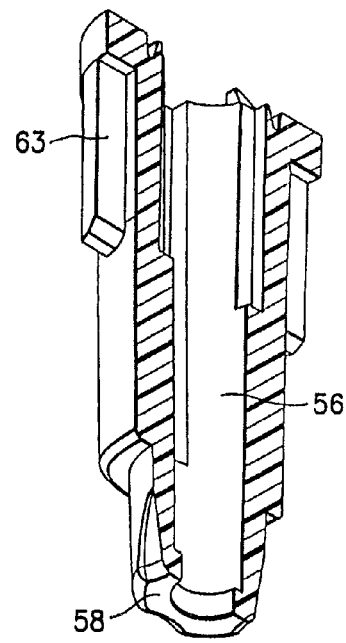
FIGS. 6B and 6C are opposing sectional views of the shield as shown in FIG. 6A.
Figure 6C:
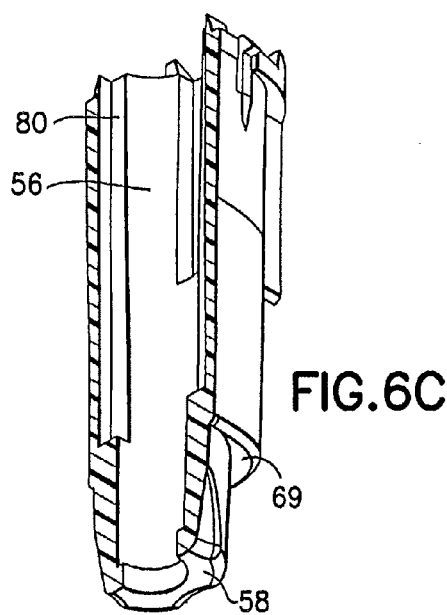
Figure 6D:
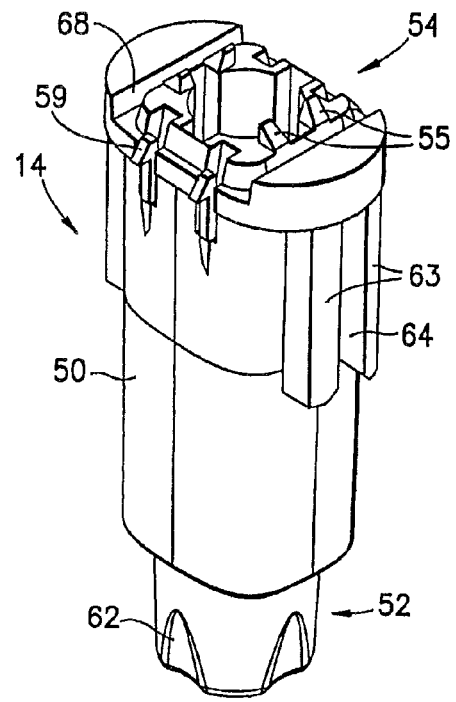
FIG. 6D is a top perspective view of the shield of FIG. 6A.
Figure 6E:
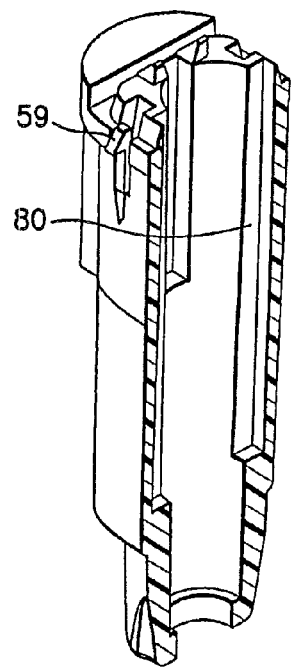
FIGS. 6E and 6F are opposing sectional views of the shield as shown in FIG. 6D.
Figure 6F:
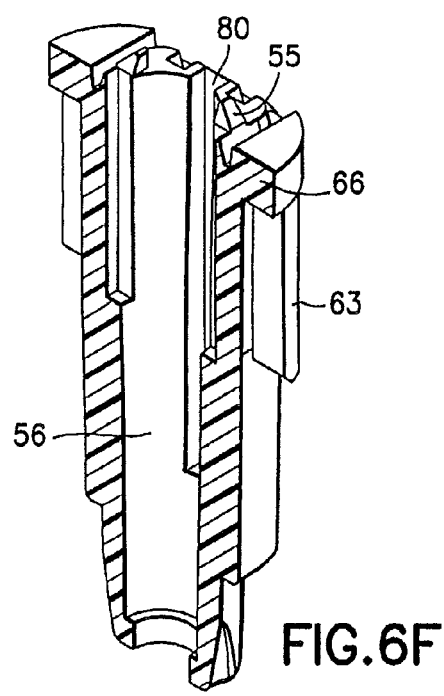
Figure 7A:
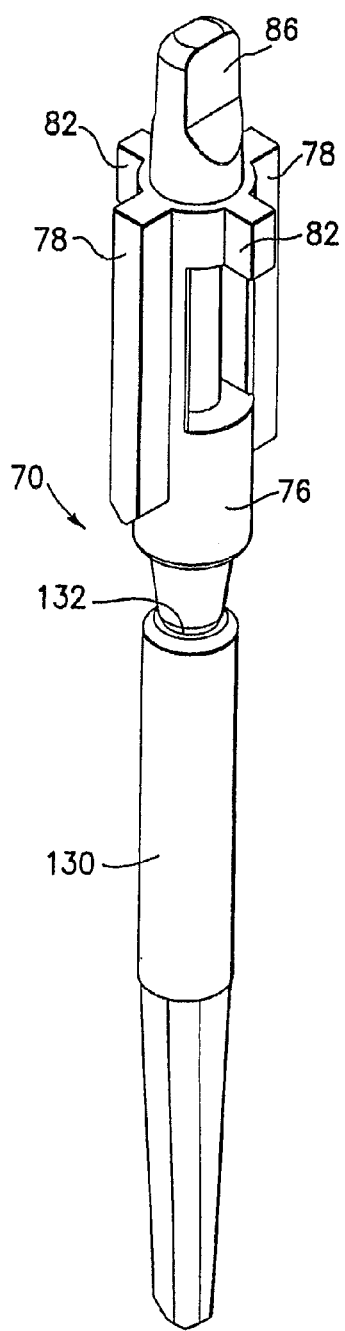
FIG. 7A is a top perspective view of the lancet structure in an embodiment of the present invention including an integrally molded cover post portion.
Figure 7B:
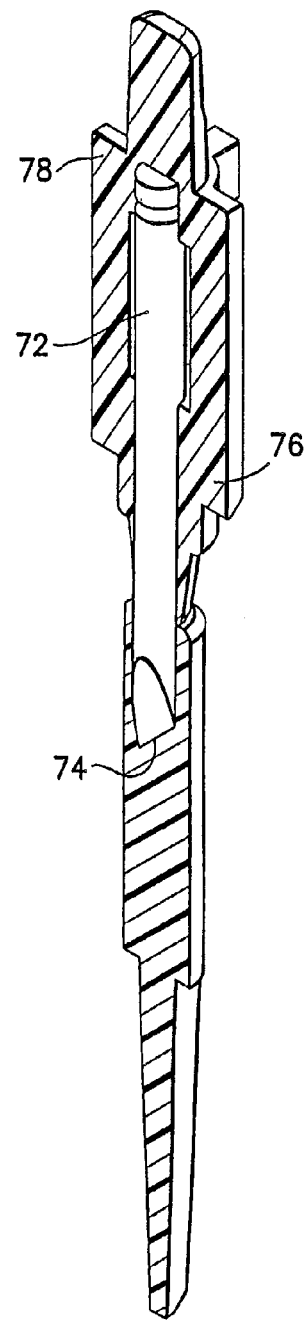
FIGS. 7B and 7C are opposing sectional views of the lancet structure as shown in FIG. 7A.
Figure 7C:
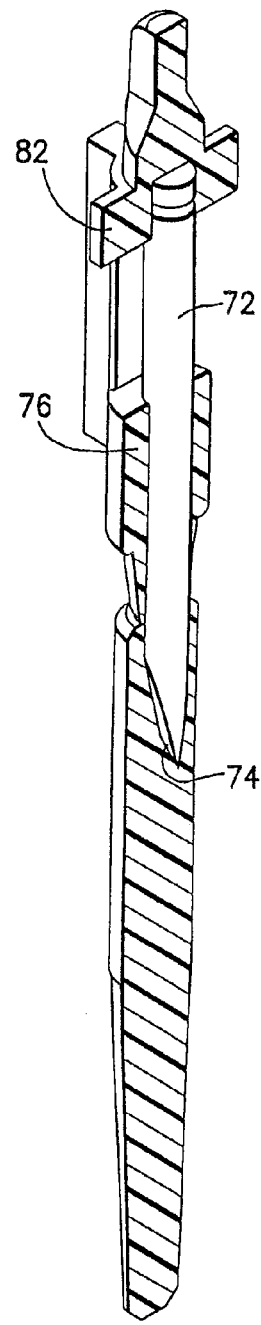
Figure 7D:
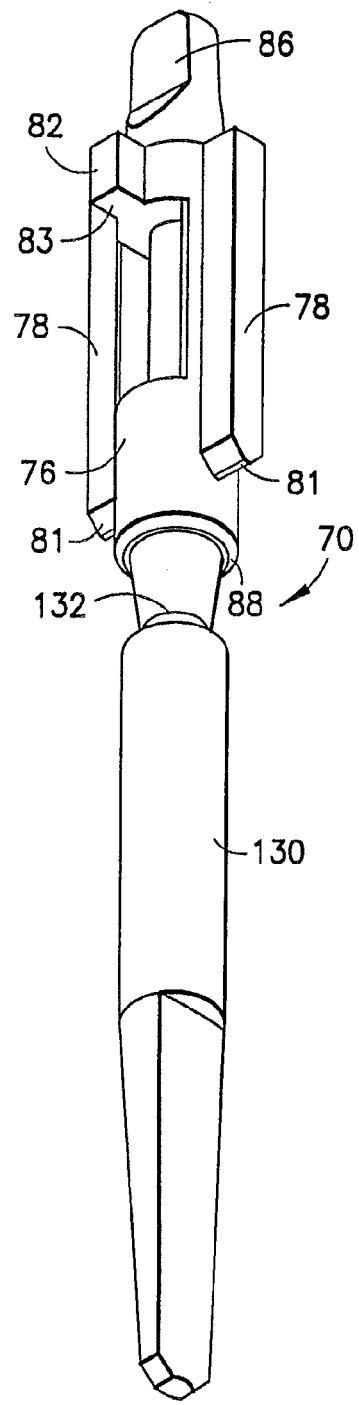
FIG. 7D is a bottom perspective view of the lancet structure of FIG. 7A.
Figure 7E:
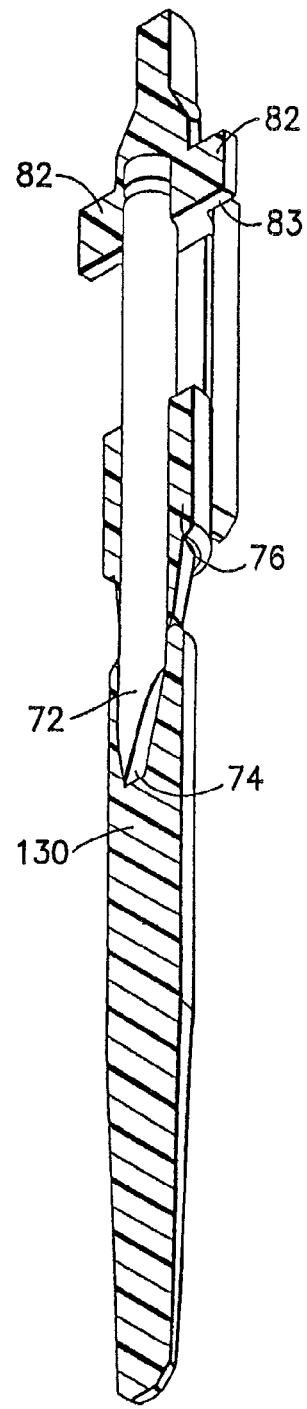
FIG. 7E is a sectional view of the lancet structure as shown in FIG. 7D.

Referring to FIGS. 1-3, a lancet device 10 according to an embodiment of the invention is generally shown. The lancet device 10 generally includes a housing 12, a shield 14 movably associated with the housing 12, and a lancet structure 70 disposed therein. As will be discussed in greater detail herein, the shield 14 is coaxially and movably associated with the housing 12, and is partially disposed within the housing 12, extending partially outward from the housing 12, with the lancet structure 70 contained within and axially or longitudinally movable through the shield 14.

The housing 12 defines an elongated body, and is desirably formed with a main body 20 defining a distal or forward end portion 22, and a rear cap 24 defining a proximal or rearward end portion 26. The interior portion of housing 12 is generally open defining internal cavity 28, which internal cavity 28 is closed at the rearward end through rear cap 24 and includes an opening 30 through the forward end portion 22, through which the shield 14 extends, as will be discussed in further detail herein. Main body 20 and rear cap 24 may be integrally formed. Alternatively, main body 20 and rear cap 24 are separate elements which are affixed to each other to form housing 12, which aids in assembly of lancet device 10. FIGS. 4A-4E and 5A-5E depict the main body 20 and rear cap 24, respectively, in an example of such an embodiment. Main body 20 and rear cap 24 may be affixed together through an appropriate adhesive, or may include inter-engaging structure providing a mechanical attachment therebetween, such as a frictional fit or a snap fit construction. For example, main body 20 may include an annular rim 31 defining an annular groove 32, and rear cap 24 may include an annular protrusion 33 having an annular lip 34 at mating surfaces thereof. When main body 20 and rear cap 24 are mated, annular protrusion 33 extends within the rear open end of main body 20, with annular lip 34 snap fitting over the annular rim 31 and into the annular groove 32 of main body 20. It should be recognized that the arrangement of such elements is merely exemplary and may be reversed, and it is contemplated that other inter-fitting engaging structure may be used to fit the main body 20 with the rear cap 24. In an alternate embodiment, main body 20 and rear cap 24 may be an integrally formed structure, and may therefore be molded together as one component.

Figure 11C:
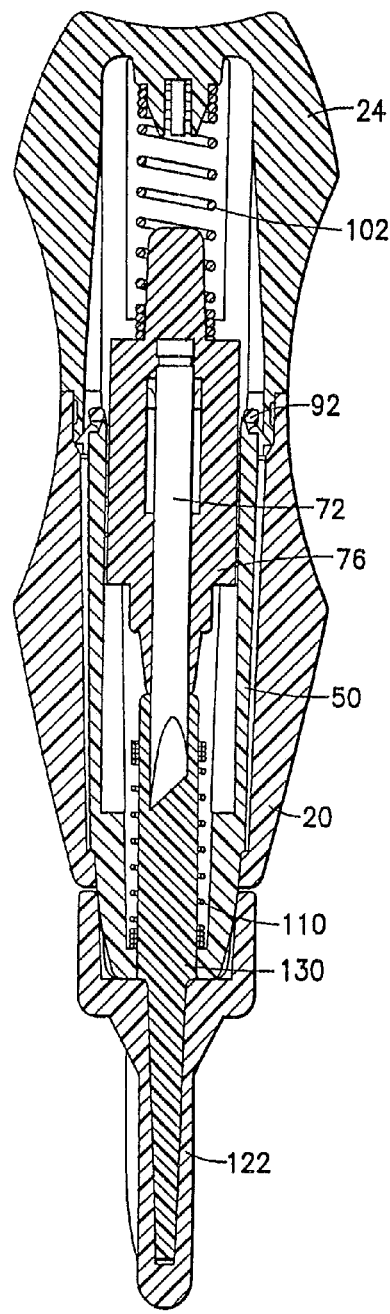
FIG. 11C is a cross-sectional view of the lancet device taken along line B-B of FIG. 11A.

As shown in FIG. 11B, the generally elongated housing 12, defined by main body 20 and rear cap 24, has opposed sides 35, 36, which may each include a surface for accommodating a user's fingers, such as finger grip indentations 37, 38. While two opposed finger grip indentations 37, 38 are provided on the housing 12, it will be appreciated that only one finger grip indentation 37 formed in the housing body 20 may be provided in accordance with the present invention. The finger grip indentations 37 may be formed as concave depressions or recesses on the outer surface of the housing 12. Additionally, the rearward end 26 of housing 12, such as the top surface of rear cap 24, may also include a surface for accommodating a user's finger, such as rear finger grip indentation 39, which may also be formed as a concave depression or recess. The side finger grip indentations 37, 38 and the rear finger grip indentation 39 provide ergonomically shaped surfaces that substantially conform to a user's fingertips to aid the user in manipulating the lancet device 10 and using the lancet device 10 in a blood letting, drawing, or collection procedure, and may provide multiple finger grip positions for the user. The side finger grip indentations 37, 38 may be represented as contours formed by a hyperbola as shown in FIG. 11B. The hyperbola, for example, may include two asymptotes that intersect at a location substantially coplanar with a plane of symmetry defining the main housing. Additionally, rear cap 24 may include a contour formed by a hyperbola, as shown in FIG. 11B. The housing 12 may further include structure to generally improve the grip between the housing 12 and the user's fingertips, such as a plurality of longitudinal ribs 40 and troughs 41 extending along the housing 12 and integrally formed with the housing 12, which may provide a visual and tactile cue to the user to instruct the user where to place his or her fingertips. The housing 12 may further include at least one and optionally two or more peripheral indentations 42 disposed at the forward end 22. In one particular embodiment, the lancet device may be constructed in accordance with the features disclosed in Application No. 60/631,795 filed Nov. 30, 2004, and entitled "Lancet Device" naming Bradley Wilkinson as inventor, the entirety of which is incorporated herein by reference thereto.

As noted above, the shield 14 extends outward from the opening 30 through the forward end of the housing 12. As shown in FIGS. 6A-6F, the shield 14 is a generally cylindrical hollow structure defining a shield body 50 extending between a forward end 52 and a rearward end 54, and defining an internal cavity 56 extending therethrough. The forward end 52 of the shield body 50 defines a forward end wall 58 including a forward opening 60 therethrough, through which the puncturing element extends when the lancet device 10 is actuated by the user, as will be discussed in more detail herein. The forward end wall 58 generally defines a small contact area about the distal opening 60 for contacting the intended area on the user's body which is to be punctured by the puncturing element. The reduced contact area may be made smaller (i.e., reduced in area) by providing a plurality of peripheral indentations 62 that are formed in the shield 14. The peripheral indentations 62 may also provide a target indicia to visually aid the user in aiming the lancet device 10 generally, and aiming the puncturing element of the lancet in particular, as will be discussed in greater detail. The peripheral indentations 62 generally resemble the peripheral indentations 42 provided on the housing 12. The peripheral indentations 42 are positioned around the perimeter of the shield 14 and may be equally spaced about the shield 14. The peripheral indentations 42 enable the user to easily visually locate the approximate discharge point of the puncturing element, thereby improving the aiming characteristics of the lancet device 10 and ensuring optimal blood flow during a skin puncturing operation.

As noted, the shield 14 is axially or longitudinally movable within the housing 12. The shield 14 and housing 12 may therefore include corresponding guiding surfaces for guiding the shield 14 through the housing 12. For example, shield body 50 may include a pair of longitudinal protrusions 63 extending along an outer surface thereof, forming guide channel 64 therebetween. Housing 12 may include corresponding structure such as a guide tab 44 within the main body 20 thereof for fitting within guide channel 64. Desirably, shield body 50 includes a pair of guide channels 64 extending longitudinally along opposing sides thereof, and housing 12 includes a pair of guide tabs 44 on opposing inner surfaces of main body 20 corresponding to each of the guide channels 64. It is contemplated that the arrangement of the guide tabs and channels may be reversed, and other guiding surfaces may also be used. The guide tabs 44 and guide channels 64 ensure that the shield body 50 is properly aligned within housing 12, and provide for sliding axial movement of the shield body 50 within the housing 12, and desirably prevent or resist rotational movement. Additionally, shield body 50 may include a ledge 66 at the rearward end thereof, for interference engagement with the top surface of guide tab 44 within main body 20 of housing 12. Alternatively or in addition thereto, shield body 50 may include a forward shoulder 69 toward the forward end thereof, and main body 20 of housing 12 may include a forward rim surface 48, providing interference engagement therebetween. Such interferingly engaging structure prevents shield body 50 from axially sliding completely out of housing 12 through opening 30.

The housing 12 and the shield 14 may further include locking structure extending therebetween, for maintaining the shield 14 in fixed relation to the housing 12 after activation. For example, shield body 50 may include structure at the rearward end 54 for frictional engagement, or for inter-fitting engagement, with the main body 20 or rear cap 24. For example, shield body 50 may include locking fingers 59 extending at the rearward end 54 thereof, for inter-fitting engagement with locking recesses 29 within the interior surface of rear cap 24.

Lancet device 10 further includes a lancet structure 70 disposed within the housing 12, and extending through shield 14. As shown in FIGS. 7A-7F, lancet structure 70 includes a puncturing element, shown in the form of lancet 72 defining a puncturing end 74 at the forward end thereof. Lancet structure 70 is adapted for axial or longitudinal movement through the internal cavity 56 of the shield body 50 between an initial armed position with the puncturing end 74 maintained within the shield body 50 to a puncturing position in which the puncturing end 74 extends beyond the forward opening 60 of shield body 50, as will be discussed further herein in terms of use of the lancet device 10.

Puncturing end 74 is adapted for puncturing the skin of a patient, and may define a pointed end, a blade edge, and the like. Puncturing end 74 may include a preferred alignment orientation, such as with a pointed end of a blade aligned in a specific orientation. In such an embodiment, shield body 50 and/or main body 20 of housing may include target indicia corresponding to the alignment orientation of the puncturing end 74. Indentations 62 of the shield body 50 and/or indentations 42 of the main body 20 may function as such an alignment orientation.

Lancet structure 70 further includes a carrier element 76 supporting lancet 72 at the rearward end thereof. The carrier element 76 and shield body 50 may include corresponding guiding surfaces for guiding the lancet structure 70 therethrough. For example, carrier element 76 may include a guide tab 78 on an external surface thereof, with the shield body 50 including a corresponding guide channel 80 extending longitudinally along an inner surface thereof for accommodating guide tab 78 slidably therein. Desirably, carrier element 76 includes a pair of guide tabs 78 on opposing lateral sides thereof, and shield body 50 includes a corresponding pair of guide channels 80 extending along opposing inner surfaces thereof corresponding to each of the guide tabs 78. It is contemplated that the arrangement of the guide tabs and channels may be reversed, and other guiding surfaces may also be used. The guide tabs 78 and guide channels 80 ensure that the lancet structure 70 is properly aligned within shield body 50, and provide for sliding axial movement of the lancet structure 70 within the shield body 50 and may prevent or resist rotational movement. A bottom surface 81 of the guide tabs 78 provides an abutment surface for abutting against a bottom surface of guide channels 80 to prevent the lancet structure 70 from axial movement entirely out of shield body 50 through forward opening 60.

Figure 10:
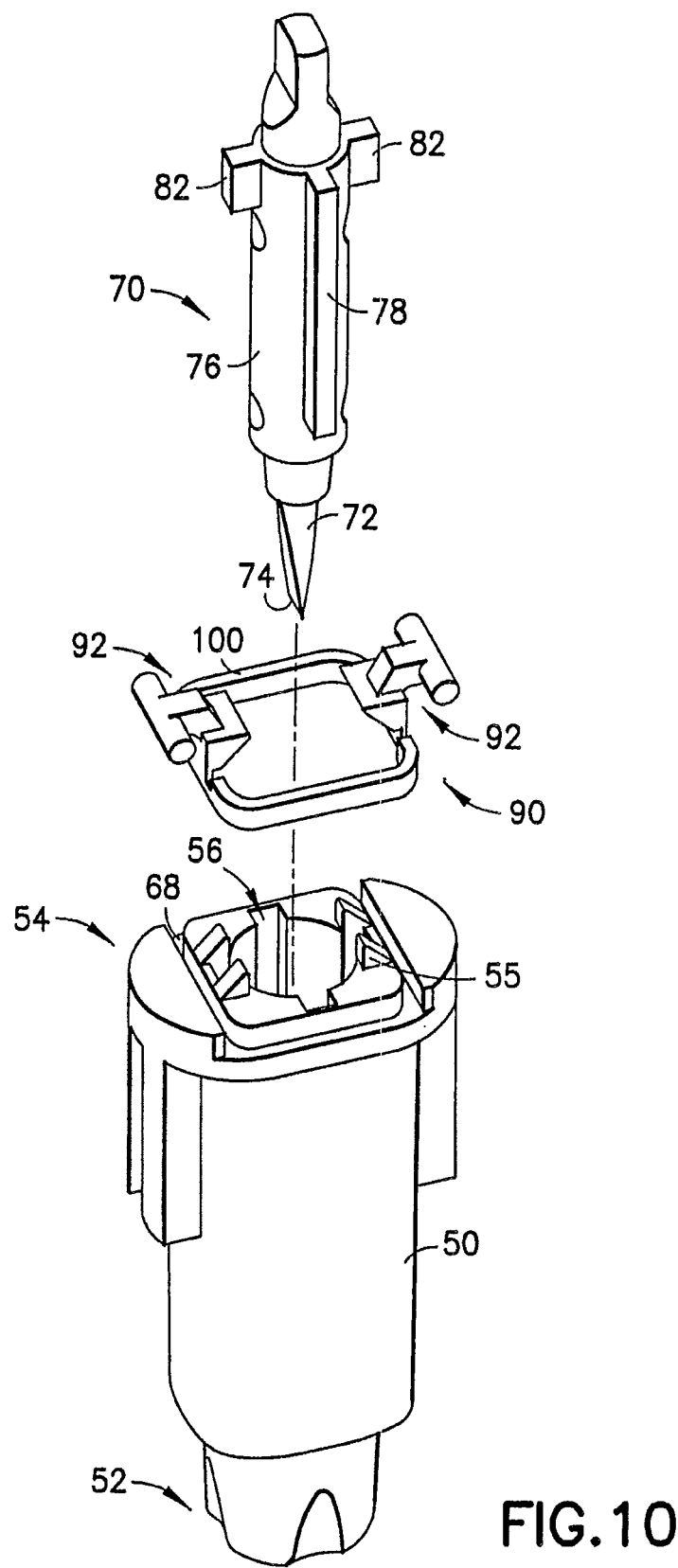
FIG. 10 is an exploded perspective view of the shield and the retaining hub with the lancet structure.

As shown in FIG. 10, retaining hub 90 is further provided, shown at the rearward end 54 of the shield body 50. Retaining hub 90 is desirably provided as a separate structure disposed or retained within the rearward end of shield body 50. For example, shield body 50 may include structure for accommodating retaining hub 90, such as recess 68 extending within an upper surface of rearward end 54. In this manner, retaining hub 90 rests within recess 68. In other embodiments, shield body 50 may include a surface for supporting and positioning retaining hub 90 to assist in assembly. Still in other embodiments of the invention, functional elements of the retaining hub 90 may be molded or formed directly onto the shield body 50.

Retaining hub 90 defines a lever structure for retaining the lancet structure 70 in an initial armed position retracted within housing 12. In particular, as shown in FIGS. 8A-8D, retaining hub 90 includes a pivotal lever element 92, including a shoulder 94 and a contact surface 96 on the upper surface thereof, with a pivot hinge 98 on the lower surface thereof between the shoulder 94 and the contact surface 96. As an example, lever element 92 defines a class 1 lever, in which the fulcrum or pivot point is positioned between the force and the load, as in a seesaw. For example, the upper surface of lever element 92 includes the shoulder 94 opposite the contact surface 96, with pivot hinge 98 providing a fulcrum between the shoulder 94 and the contact surface 96. In this manner, the load, represented by the lancet structure 70 resting on the shoulder 94, is separated from the force, which is applied at the contact surface 96 as will be described in more detail herein, with the fulcrum of pivot hinge 98 located between the force and the load.

As depicted in FIGS. 8A-8D, lever element 92 may be provided, in one embodiment, as a pivotal generally wedge-shaped structure, with the bottom point of the wedge acting as the fulcrum at pivot hinge 98 for pivotal movement of the lever. The retaining hub 90 may include an annular rim 100, with at least one lever element 92 supported on and pivotally hinged to the annular rim 100 through the pivot hinge 98. Retaining hub 90 typically includes a pair of lever elements 92 pivotally hinged to the upper surface of the annular rim 100 at opposing sides thereof. Annular rim 100 is depicted herein as a generally rectangular ring-like structure with curved corner connections, extending circumferentially or perimetrically to define an interior opening. The term "annular" as used herein is intended to encompass any ring-like or band-like structure, whether circular, curved, or polygonal, including curved or angular corner connections. It is also contemplated that other annular yet incomplete rings or band-like structures may be used, such as a structure similar to a slotted or slip-on washer, which has a discontinuous annular structure.

Retaining hub 90 and lancet structure 70 are in interference engagement with each other, such that retaining hub 90 retains the lancet structure 70 in an initial armed position retracted within housing 12. For example, carrier element 76 may include a finger 82 extending laterally therefrom, including a support surface 83 on a bottom surface of the finger 82. Support surface 83 of finger 82 rests on shoulder 94 of lever element 92, thereby providing interference engagement between the lancet structure 70 and the retaining hub 90.

Moreover, contact surface 96 of lever element 92 is adapted for contacting engagement with structure within housing 12. For example, rear cap 24 of housing 12 may include structure extending therein, such as internal contact 46 integrally formed and extending on at least one, and desirably on two opposing inner sidewalls thereof. Each internal contact 46 includes an engagement surface 47 for contacting engagement with contact surface 96 of lever element 92, forming a cam surface. In one embodiment, contact surface 96 includes a generally rod-shaped portion 97, and the internal surface of rear cap 24 includes a pair of internal contacts 46 extending adjacent each other on the inner wall surface, and on each opposing side of the inner wall surface. In this manner, the pair of internal contacts 46 engages opposing ends of the rod shaped portion 97 of contact surface 96, thereby providing a continual cam-like contact surface around the perimeter of the rod shaped portion 97 during pivotal movement of lever element 92. In an alternate embodiment shown in FIG. 8E, contact surface 96 may include angular surfaces 197 forming a chamfered portion as opposed to the generally rod-shaped portion discussed above. Such a chamfered portion formed by angular surfaces 197 is particularly useful in molding operations for forming of the retaining hub 90 in conventional injection molding procedures. With such an embodiment, the pair of internal contacts 46 within rear cap 24 engages opposing ends of the chamfered portion formed by the angular surfaces 197 of contact surface 96, providing for a cam-like contact surface as noted above.

Figure 8A:
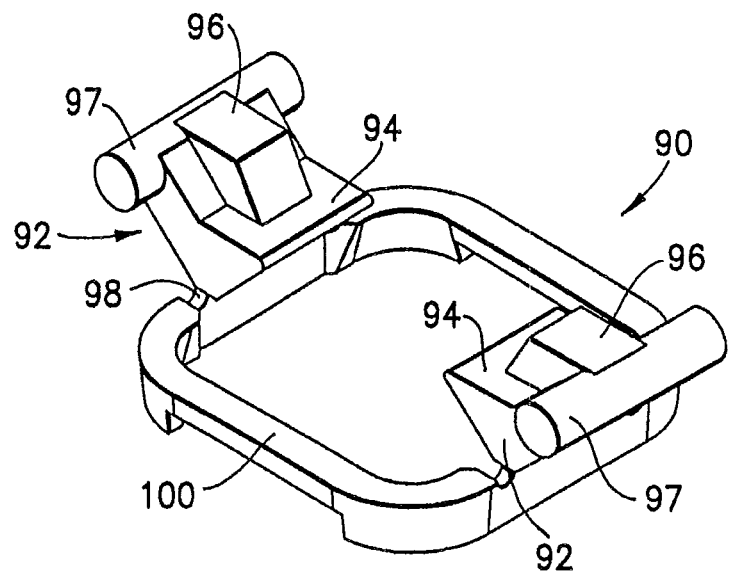
FIG. 8A is a top perspective view of the retaining hub in an embodiment of the present invention.
Figure 8B:
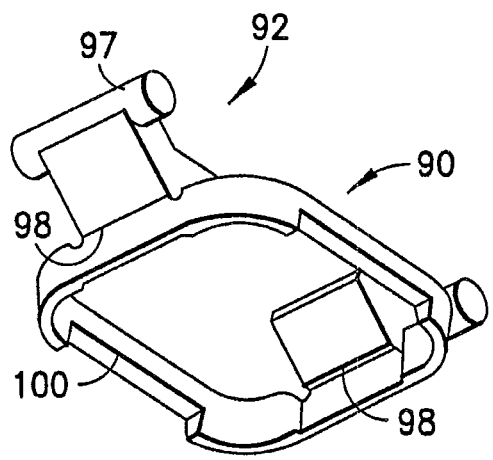
FIG. 8B is a bottom perspective view of the retaining hub of FIG. 8A.
Figure 8C:
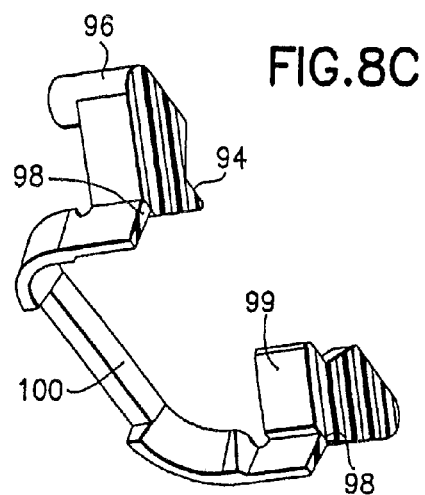
FIG. 8C is a sectional view of the lancet structure as shown in FIG. 8B.
Figure 8D:
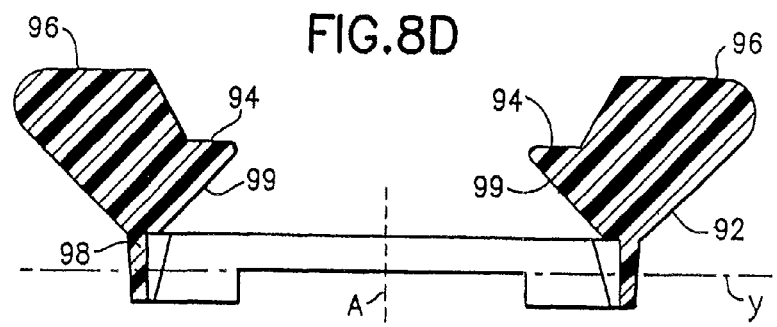
FIG. 8D is a cross-sectional view of the lancet structure as shown in FIG. 8B.
Figure 8E:
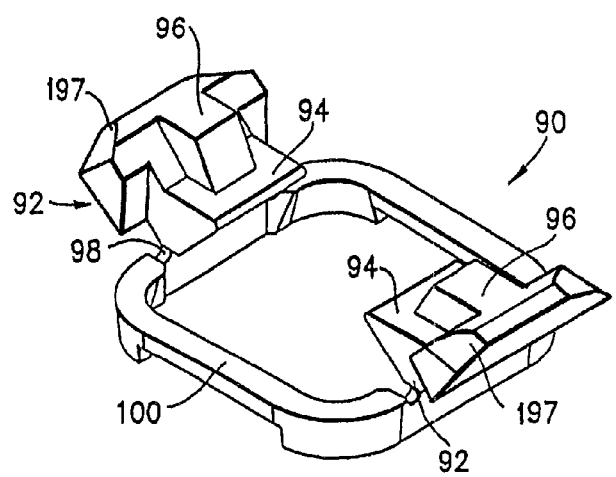
FIG. 8E is a top perspective view of a retaining hub in an alternate embodiment.
Figure 9A:
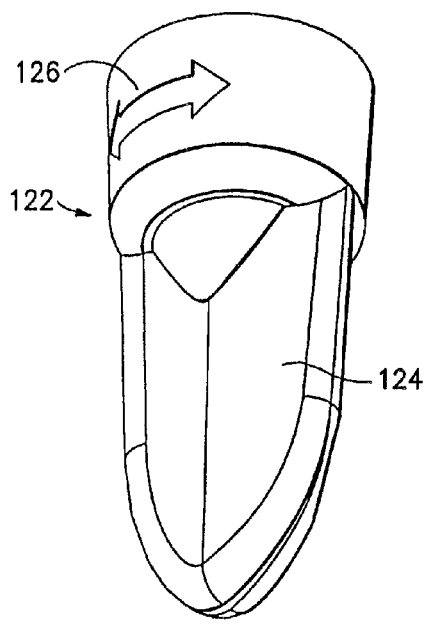
FIG. 9A is a bottom perspective view of the tab member in an embodiment of the present invention.
Figure 9B:
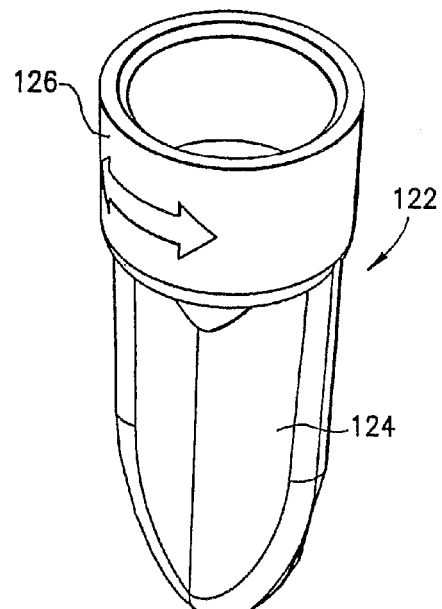
FIG. 9B is a top perspective view of the tab member of FIG. 9A.
Figure 9C:
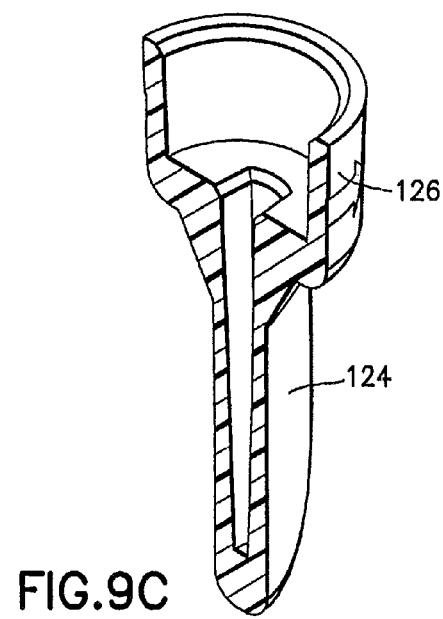
FIGS. 9C-9F are opposing sectional views of the tab member as shown in FIGS. 9A-9B.
Figure 9D:
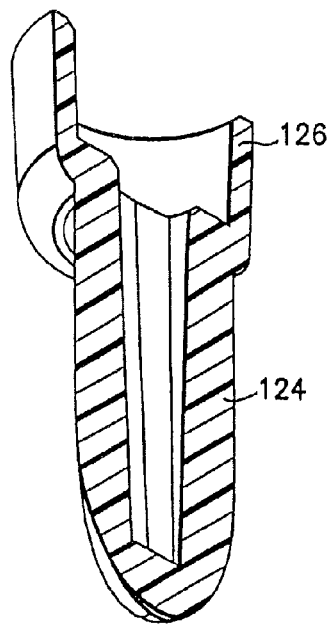
Figure 9E:
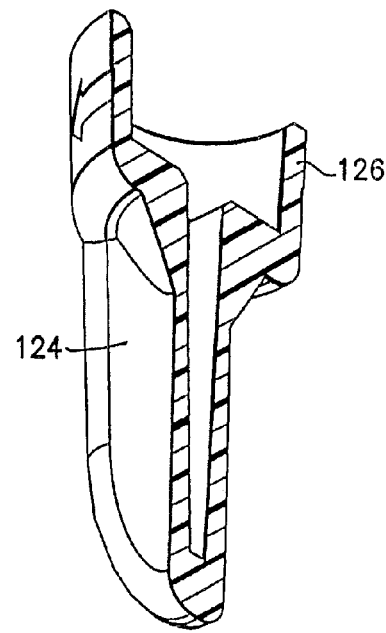
Figure 9F:
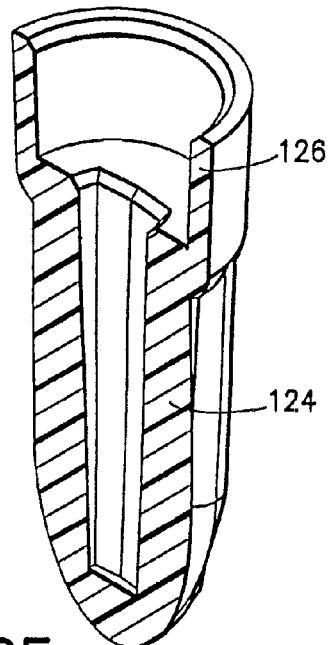

Moreover, lever element 92 is typically positioned on one side of a plane, shown in FIG. 8D at plane Y, dissecting the annular rim 100 at a cross section to the general longitudinal axis A which generally defines the lancet device 10 and the direction of travel of lancet structure 70. In this manner, the fulcrum, such as that defined through pivot hinge 98, represents a low area moment of inertia above the plane Y, such as at the top surface of annular rim 100, to cause plastic deformation of lever element 92, and namely pivot hinge 98, as the lever element 92 pivots outwardly. Such plastic deformation may be permanent, such that after the lever elements pivot, they maintain their shape and position.

Movement of the lancet structure 70 through the lancet device 10 is achieved through a biasing force provided through a drive spring 102. Drive spring 102 is adapted to exert a biasing force against lancet structure 70 to drive lancet structure 70 through the device toward the puncturing position, and may be disposed between the rearward end of the housing 12 and the lancet structure 70. Drive spring 102 may be a separate element contained between the rearward end of housing 12 and the lancet structure 70, or may be integrally formed with one or both of housing 12 and/or lancet structure 70. Rear cap 24 may include structure for alignment of and/or for maintaining drive spring 102 in the proper orientation. For example rear cap 24 may include an alignment nub 104 for accommodating the drive spring 102. The lancet structure 70 may also include a surface or structure for accommodating an opposing end of the drive spring 102, such as a rear nub 86 extending from the carrier element 76 of lancet structure 70. Drive spring 102 extends between alignment nub 104 of rear cap 24 and rear nub 86 of carrier element 76. When the lancet structure 70 is in an armed position, the drive spring 102 exerts a force against the lancet structure, such as between the rearward end of housing 12 and the lancet structure 70, biasing the lancet structure 70 toward the puncturing position. The shield body 50 and lever element 92 may include inter-engaging structure to prevent lever element 92 from pivoting in a reverse direction about pivot hinge 98, regardless of the biasing force applied against lancet structure 70 and shoulder 94 through drive spring 102. For example, bottom angled surfaces 99 formed from the wedge-shaped lever element 92 may engage and abut corresponding angled nibs 55 on the rearward end 54 of shield body 50. Such inter-engaging surfaces prevent any applied force from drive spring 102 from pivoting the lever element 92 about pivot hinge 98 in a reverse direction, that is in a direction such that shoulder 94 pivots downwardly into interior cavity 56 of shield body 50. Optionally or in addition thereto, the plastic deformation of pivot hinge 98 as discussed above may be permanent, thereby preventing lever element 92 from automatically pivoting in a reverse direction to enable the lancet structure 70 to be re-set in a pre-actuation state resting on shoulder 94 after actuation.

A retraction spring 110 may further be provided at the forward end of the lancet device 10, for retracting the lancet structure 70 within the shield body 50 after the lancet structure 70 is axially moved to the puncturing position. Retraction spring 110 typically extends between a forward surface 88 of the carrier element 76 of lancet structure 70 and an inner surface within the forward end wall 58 of the shield body 50. Retraction spring 110 is typically a compression spring, capable of storing energy when in a compressed state.

Lancet device 10 may further include a protective cover 120 for protectively covering the lancet device 10 prior to use thereof. The protective cover 120 may include a tab member 122 associated with the forward end of the lancet device 10, which maintains sterility of the forward end wall 58 of shield body 50. Referring to FIGS. 9A-9F, tab member 122 may include a forward tab portion 124 and a depending skirt 126. The depending skirt 126 is adapted to cooperate with the forward end 52 of the shield body 50, generally encompassing or enclosing the forward end 52. The depending skirt 126 also contacts the forward end 22 of the main body 20 of the housing 12. In this manner, the tab member 122 encloses forward opening 30 of main body 20 and forward opening 60 of shield body 50. Moreover, such arrangement maintains the respective forward ends of main body 20 and shield body 50 in fixed relation with respect to each other, thereby preventing movement therebetween which could cause premature activation of the lancet device 10.

Figure 11D:
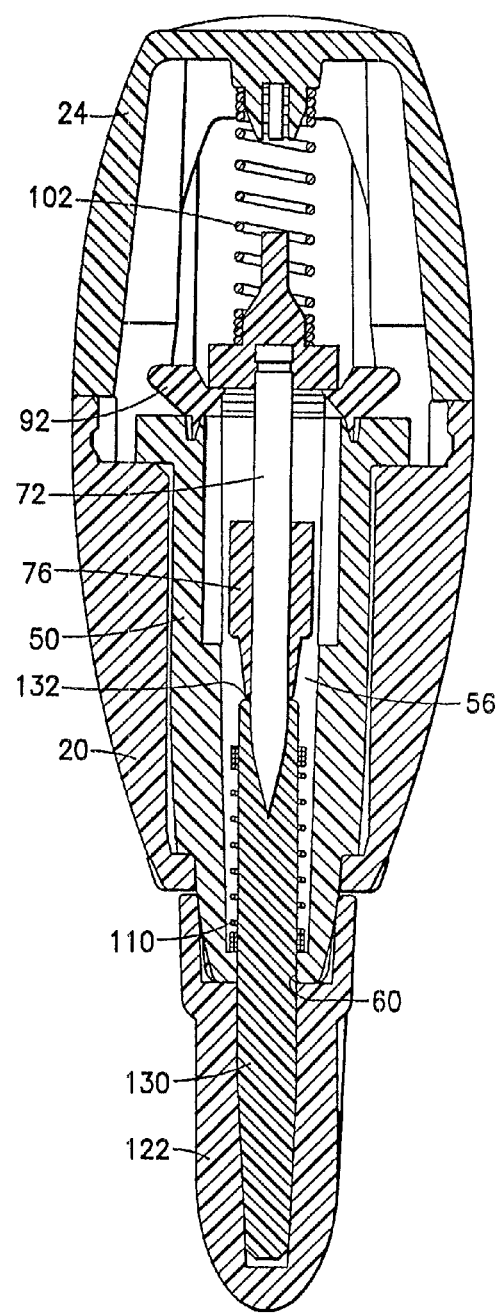
FIG. 11D is a cross-sectional view of the lancet device taken along line A-A of FIG. 11B.
Figure 12:
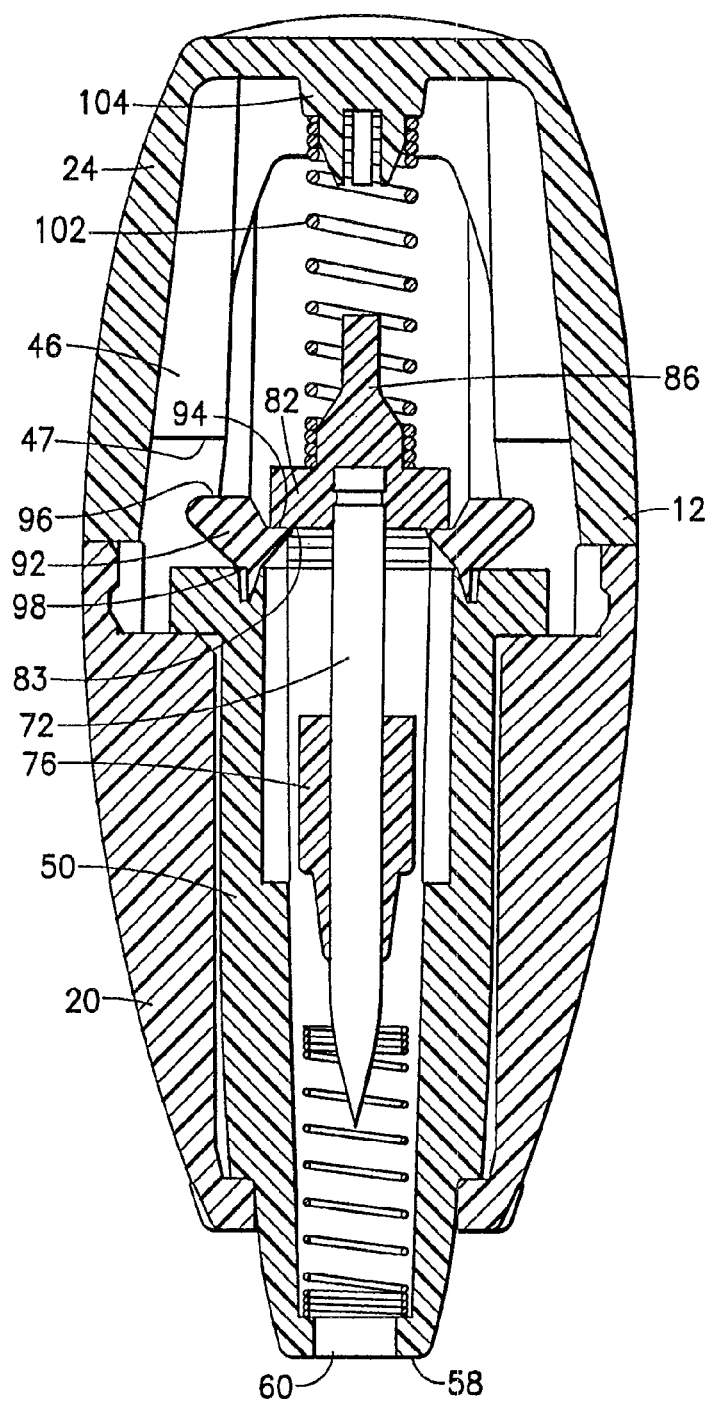
FIG. 12 is a cross-sectional view of the lancet device of FIG. 11D with the tab member removed and ready for use.

A portion of the protective cover 120 may extend within the shield body 50 to encompass at least a portion of the puncturing element. For example, as shown in FIG. 11D, a post portion 130 extends through forward opening 60 of shield body 50 and into internal cavity 56 thereof, protectively surrounding and encompassing at least a portion of the puncturing element, namely lancet 72. The post portion 130 and tab member 122 may be separate elements which are affixed or otherwise maintained together. For example, tab member 122 may include an inner opening for accommodating post portion 130 therethrough. Referring generally to FIGS. 7A-7E, post portion 130 may be formed integrally with carrier element 76 of lancet structure 70, completely encompassing lancet 72, thereby maintaining sterility thereof prior to use. Post portion 130 and carrier element 76 may include a notched portion 132 at a juncture therebetween, providing a fraction point for removing post portion 130 and exposing lancet 72. Alternatively, the post portion 130 may be secured directly to the lancet 72 by methods customary in the medical field, such as with a releasable medical grade adhesive.

In one embodiment, the rear cap 24 and the housing body 20 are separate structures which are mated, with the housing body 20 forming a forward portion of the housing 12 and the rear cap 24 forming a substantial rear portion of the housing 12. More particularly, the rear cap 24 may constitute a significant portion of the housing 12, such as approximately half of the housing 12, mating with the housing body 20 at a location dividing housing 12 approximately in half when measured by the complete longitudinal length of the housing and rear cap together. Such an arrangement provides for simplified assembly of the lancet device 10, in that the internal components including shield 14, lancet structure 70, and the retaining and engaging elements including retaining hub 90, drive spring 102 and optionally retraction spring 110, may be inserted within the housing body 20 from the rearward end thereof, requiring little clearance provided by the small size of housing body 20 for insertion. Additionally, after inserted as such, such internal elements may be easily seen due to the low clearance provided by the relative small size housing body 20 with respect to the overall housing 12, thereby permitting easy visual assurance of proper alignment. Moreover, the rear cap 24 may then be fitted to housing body 20 at a location adjacent the internal functional components, such as at a location substantially peripheral to the retaining hub 90 within the housing 12. Also, the housing body 20 and the rear cap 24 may mate at a substantial midpoint of the total length of the housing 12, with each substantially defining a half portion of the housing 12. In this manner, the mating of the housing body 20 and the rear cap 24 substantially intersects or bisects the finger grip indentations 37, 38.

The respective elements of the lancet device of the present invention are all typically formed of molded plastic material, such as a medical grade plastic material. The lancet 72 may be constructed of any suitable material adapted for puncturing the skin, and is typically a surgical grade metal such as stainless steel.

Use of the lancet device 10 will now be described with general reference to FIGS. 1-18, and particular reference to FIG. 11D and FIGS. 12-18. Prior to use, lancet device 10 is provided as shown in FIGS. 1 and 11D, with protective cover 120 covering shield 14 at the forward end thereof. Lancet device 10, and in particular lancet structure 70, is in an initial pre-actuation state, with finger 82 of carrier element 76 abutting or resting upon shoulder 94 of the lever element 92 in interference engagement therewith. In this manner, lever element 92 of the retaining hub 90 maintains lancet structure 70 in this pre-actuation position within housing 12, and in particular with puncturing end 74 maintained retracted within shield body 50. Further, drive spring 102 extends between the lancet structure 70 and the rear cap 24 of housing 12. In this pre-actuation position, drive spring 102 may be in a relaxed state or may be in a fully compressed state. More desirably, drive spring 102 is in a partially compressed state in this pre-actuation position, exerting a biasing force between rear cap 24 and lancet structure 70, with the interference engagement between finger 82 and shoulder 94 maintaining lancet structure 70 against any such biasing force. Moreover, the inter-engaging surfaces between bottom angled surfaces 99 and angled nibs 55 prevent lever element 92 from pivoting in a reverse direction, thereby forcing lancet structure 76 through shield body 50. Also, in this state, protective cover 120 prevents any axial movement of shield 14 with respect to housing 12, thereby preventing actuation of the lancet device 10.

To prepare the lancet assembly for use, the user grasps housing 12, such as between a finger and thumb on opposing sides 35, 36, and removes the protective cover 120 from the forward end as shown in FIG. 2, thereby exposing the shield body 50 extending from the forward end of main body 20 of housing 12. The forward tab portion 124 of the tab member 122 may be ergonomically formed, such as through the inclusion of a paddle-shaped member, to allow the user to easily manipulate the tab member 122 and apply the necessary force or torque to release the depending skirt from frictional engagement with the forward end of the shield body 50, and to break the post portion 130 from the carrier element 76 at the notch 132 to thereby release the post portion 130 from the lancet 72. The applied breaking force is in accordance with the present invention and may be a singular twisting or pulling motion, or a combined "twisting" (i.e. rotational) and "pulling" motion applied for breaking the connection between the post portion 130 and the carrier element 76, as well as to release the frictional engagement between the depending skirt 126 and the shield body 50.

Figure 13:
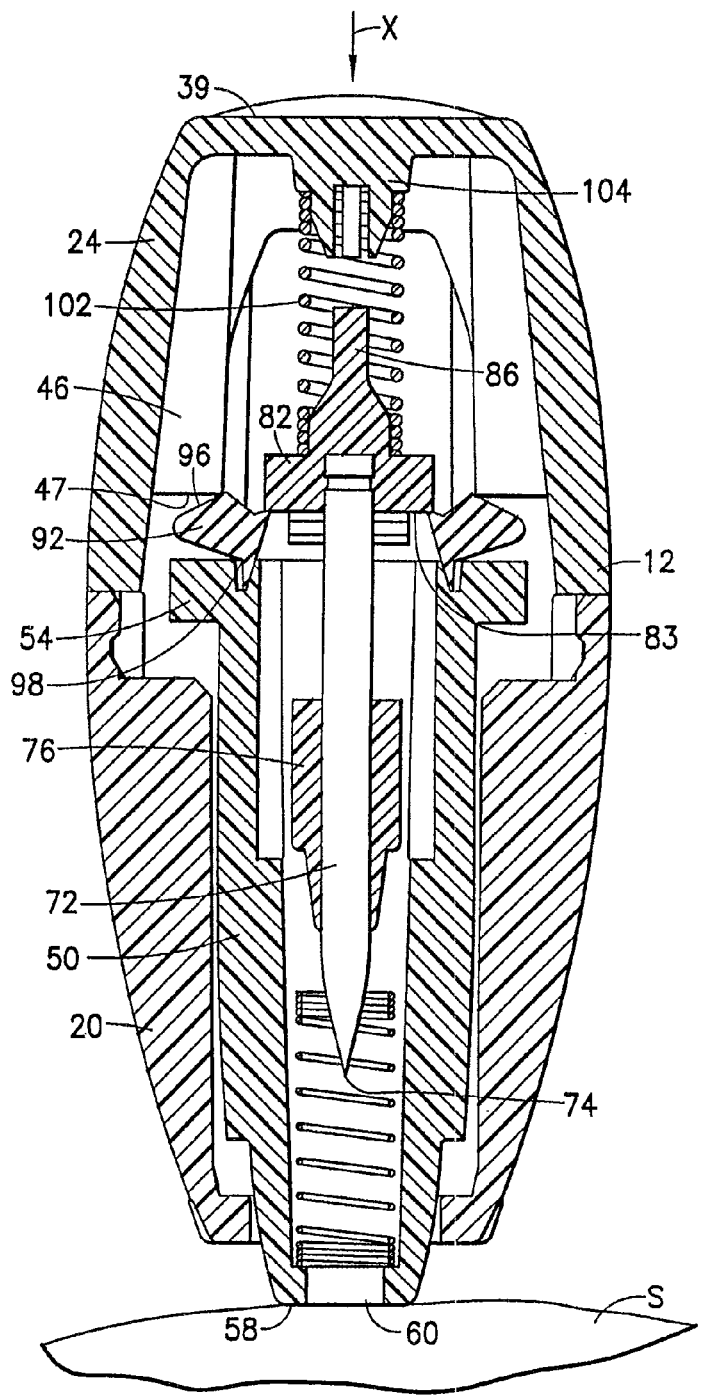
FIG. 13 is a cross-sectional view of the lancet device of FIG. 11D in use, with the lever partially engaged.

The forward end wall 58 of shield body 50 may then be contacted with a location on the user's body or another person's body where it is desired to initiate blood flow, such as the patient's skin surface S as shown in FIG. 13. If provided, target indicia, such as indentations 62, may be aligned with the desired location of puncture.

Once placed against the body, the user exerts a downwardly directed force on the housing 12 forcing shield body 50 against skin surface S. In particular, the user applies a force against the finger grip indentation 39 of the rear cap 24 in the direction of Arrow X, thereby applying a force against the skin surface S. Such force establishes an opposing external pressure force between the forward end wall 58 of the shield body 50 and the rear cap 24 of the housing 12 causing the shield body 50 to move axially within the housing 12, thereby displacing the rearward end 54 of the shield body toward the rear cap 24. The corresponding guiding surfaces provided through guide tabs 44 and guide channels 64 guide the shield body 50 axially through the main body 20 of housing 12, ensuring proper axial alignment therebetween.

Since retaining hub 90 is adjacent rearward end 54 of shield body 50, such displacement of the rearward end 54 of the shield body toward the rear cap 24 causes corresponding rearward movement of retaining hub 90 toward rear cap 24. Moreover, the interference engagement between shoulder 94 of lever element 92 of retaining hub 90 and finger 82 of carrier element 76 of lancet structure 70 causes corresponding rearward movement of lancet structure 70 toward the rear cap 24. Such movement causes drive spring 102 to compress. In embodiments in which drive spring 102 is in a relaxed state in the initial pre-actuated position, this compressing of drive spring 102 arms drive spring 102 with a biasing force sufficient to propel lancet structure 70 axially forward through shield body 50 to the puncturing position, thereby providing lancet structure 70 in an armed position. At this point, however, lancet structure 70 is still maintained such that puncturing end 74 is retracted within shield body 50 due to the interference engagement between finger 82 and shoulder 94. In embodiments in which drive spring 102 is in a partially compressed state in the initial pre-actuated position, this compressing of drive spring 102 further aims drives spring 102 with additional biasing potential energy sufficient to fully propel lancet structure 70 axially forward through shield body 50 to the puncturing position. Again, in this pre-actuated armed position, lancet structure 70 is still maintained such that puncturing end 74 is retracted within shield body 50 based on the interference engagement between finger 82 and shoulder 94.

Figure 14:
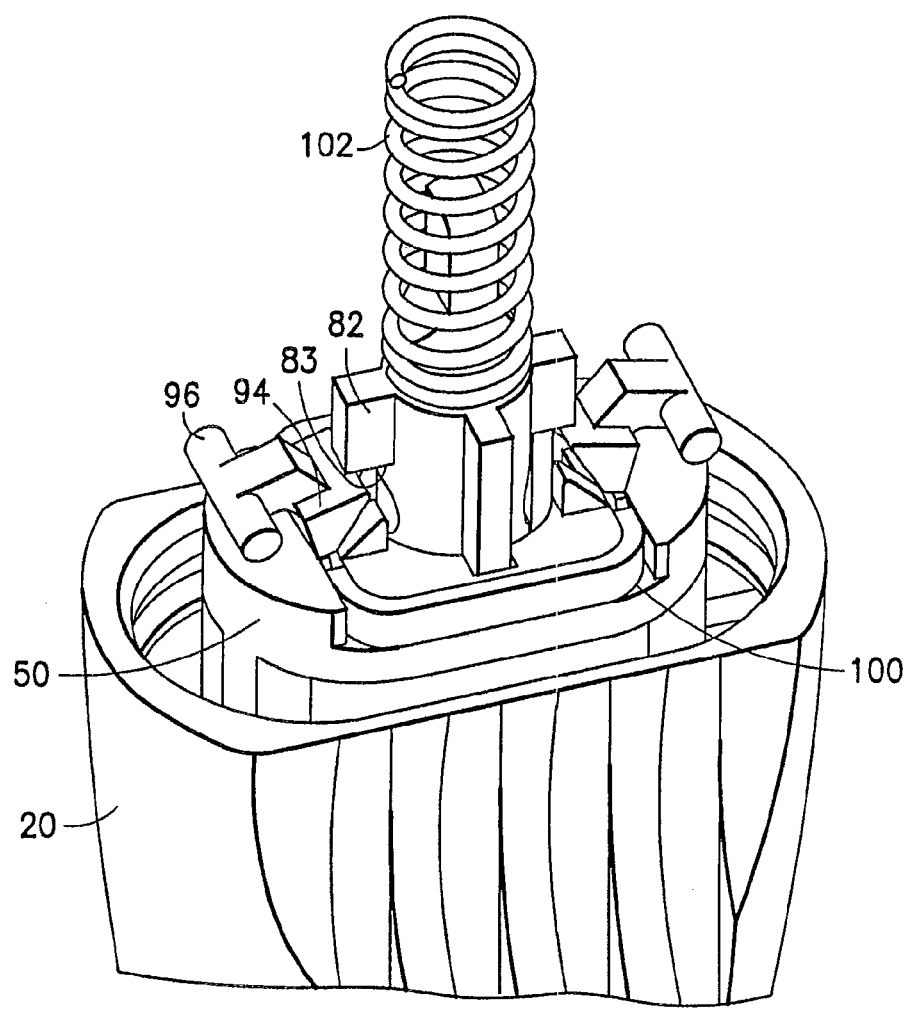
FIGS. 14-15 are partial enlarged perspective views of the lancet device of FIG. 11D during use, with the rear cap removed.

During such axial or longitudinal movement of shield body 50 toward rear cap 24, the retaining hub 90 is also displaced rearwardly (or proximally) toward rear cap 24, with fingers 82 of the carrier element 76 resting upon shoulders 94 of the lever elements 92. As shown in FIGS. 13-14, such rearward movement of retaining hub 90 causes the cam surfaces of engagement surfaces 47 of the internal contacts 46 within rear cap 24 to engage and co-act with the corresponding contact surfaces 96 of lever elements 92, such as the rod shaped portions 97. Accordingly, the corresponding camming contact surfaces provide an actuator element for the lancet device 10. Such engagement and co-action causes the lever elements 92 to pivot about pivot hinges 98 with respect to annular rim 100 due to the wedge-shaped profile of the lever elements 92. In particular, with the shoulders 94 extending generally radially inwardly of the annular rim 100 and the contact surfaces 96 generally on an external perimeter of the annular rim 100, engagement surfaces 47 engage the contacting surfaces 96, and in particular the rod shaped portions 97, at an external perimeter of the annular rim 100, thereby pivoting the lever element 92 about the fulcrum of pivot hinge 98 by tipping the contact surfaces 96 and the shoulders 94 to release the lancet structure through the annular rim 100 and into the internal cavity 56 of the shield body 50.

Figure 15:
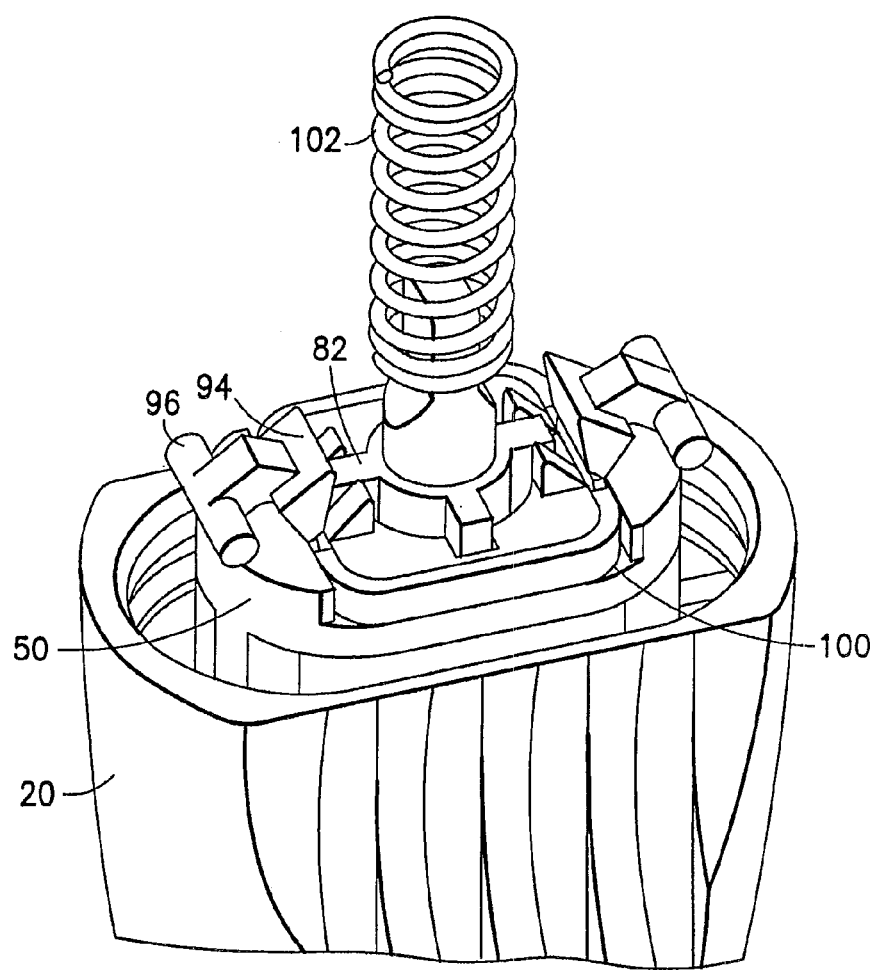
Figure 16:
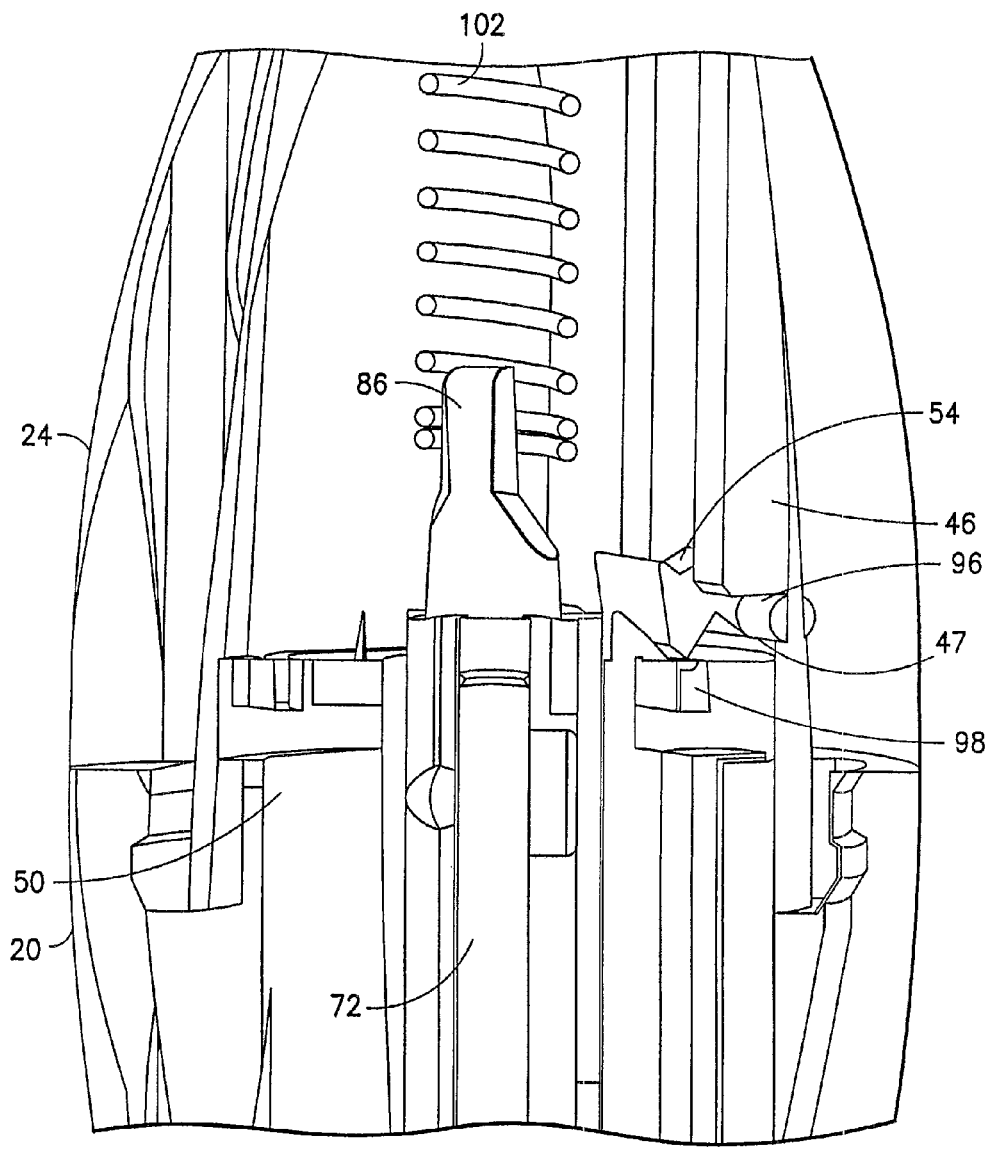
FIG. 16 is a partial enlarged cut-away view of the lancet device in use in the position shown in FIG. 15.

Such engagement provides for actuation of the lancet device. In particular, the pivoting of lever elements 92 about pivot hinges 98 further displaces shoulders 94 toward the rearward end of rear cap 24, thereby further compressing and further biasing drive spring 102. Continued axial displacement of shield body 50 toward rear cap 24 causes further engagement of the corresponding surfaces of internal contacts 46 and contact surfaces 96, such that engagement surfaces 47 cam or ride about the perimeter of rod-shaped portions 97, thereby further pivoting lever elements 92. Eventually, such pivoting causes shoulders 94 to be pivoted to a point at which the interference engagement between shoulders 94 and fingers 82 of carrier element 76 is released, as shown in FIGS. 15-16. At this point, fingers 82 are free from shoulders 94 and may axially move through the internal opening through annular rim 100. The biasing force of drive spring 102 propels lancet structure 70 downward away from the rear cap 24 axially through housing 12 and shield body 50. During such movement, corresponding guide tabs 78 and guide channels 80 guide lancet structure 70 axially through shield body 50. Moreover, shield body 50 may further include additional channels in alignment with and adapted for accommodating fingers 82 of lancet structure 70 in sliding relation during such axial movement therethrough.

Actuation of the lancet device 10 is therefore achieved through the interfering or camming engagement contact between the engagement surfaces 47 and contact surfaces 96, providing the pivoting movement of lever element 92. As noted, such pivoting movement results in both compression of drive spring 102 to arm or to further arm the lancet structure 70 and sequential release of the interference engagement maintaining the lancet structure 70 in the pre-actuated or armed position. Accordingly, actuation of the lancet device 10 achieves sequential arming and release of the lancet structure through a single motion of the device. Moreover, such sequential arming and release merely requires movement of the inter-engaging contact surfaces between the housing 12 and the pivoting lever element 92. It is therefore contemplated that such sequential arming and release may be attained regardless of whether an axially moveable shield is included, so long as some mechanism for movement of the inter-engaging surfaces with respect to each other is provided.

Figure 19:
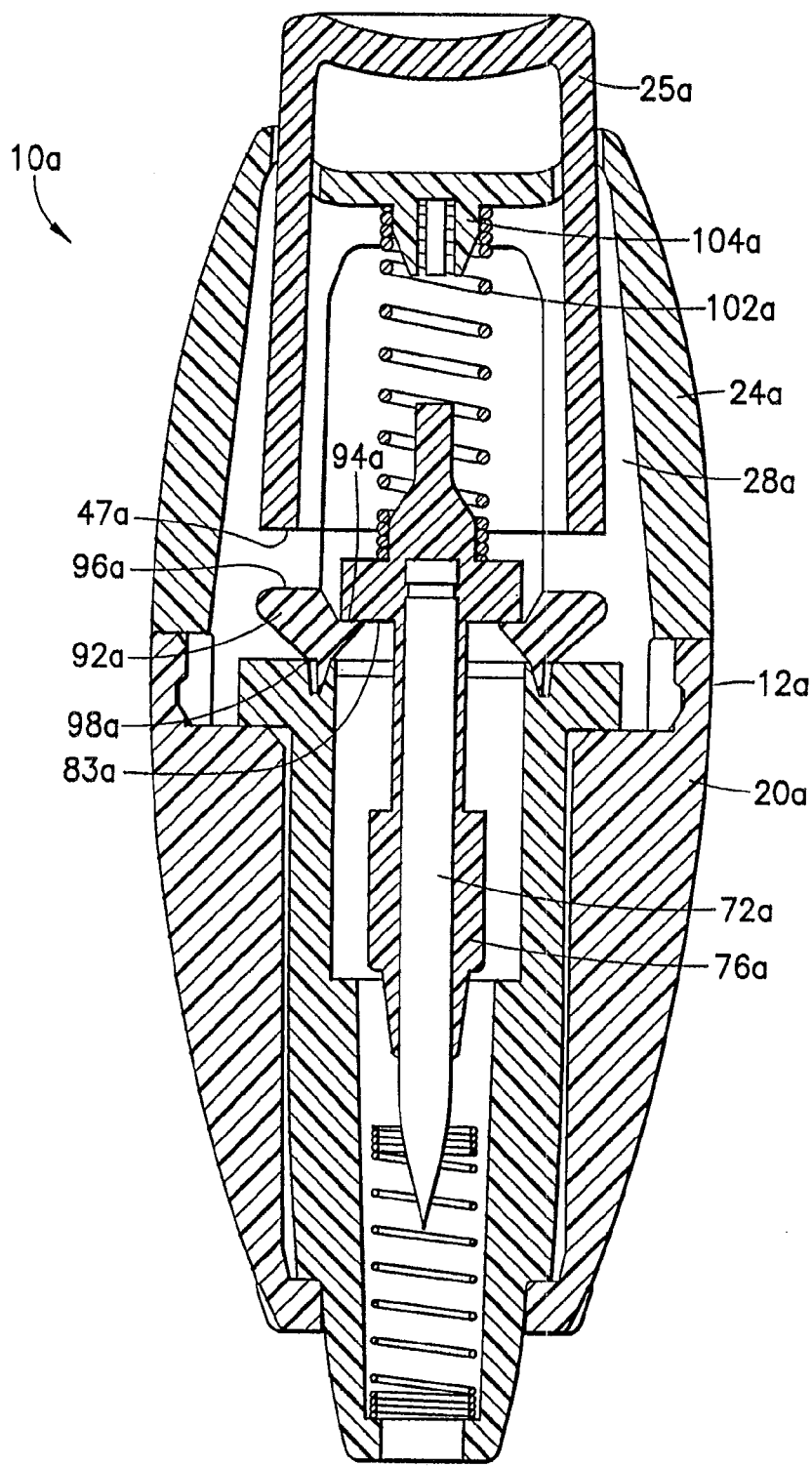
FIG. 19 is a cross-sectional view of a lancet device in an alternate embodiment of the present invention.

For example, FIG. 19 depicts a cross-sectional view of a lancet device 10a in an alternate embodiment of the present invention. In this embodiment, actuation is achieved through an actuator including an actuation element, such as push button 25a. In particular, housing 12a is defined by main body 20a and rear cap 24a. Push button 25a extends through housing 12a at rear cap 24a, and into the internal cavity 28a therein. Actuation of lancet device 10a is accomplished by axially moving push button 25a within housing 12a, such that one or more engagement surfaces 47a at the forward end of push button 25a within housing 12a contact the corresponding contact surface(s) 96a of lever element 92a, thereby pivoting the lever element 92a about pivot hinge 98a. As in the aforementioned embodiment, such contacting and pivoting releases the interference engagement between the support surface 83a of carrier element 76a and the shoulder 94a of lever element 92a, thereby permitting drive spring 102a to propel lancet 72a through housing 12a to the puncturing position. Drive spring may be maintained between carrier element 76a and push button 25a through alignment nub 104a within push button 25a. Alternatively, the drive spring may be maintained between the carrier element and the rearward end of the housing, with the push button element extending through the housing to cause pivotal actuation.

Figure 17:
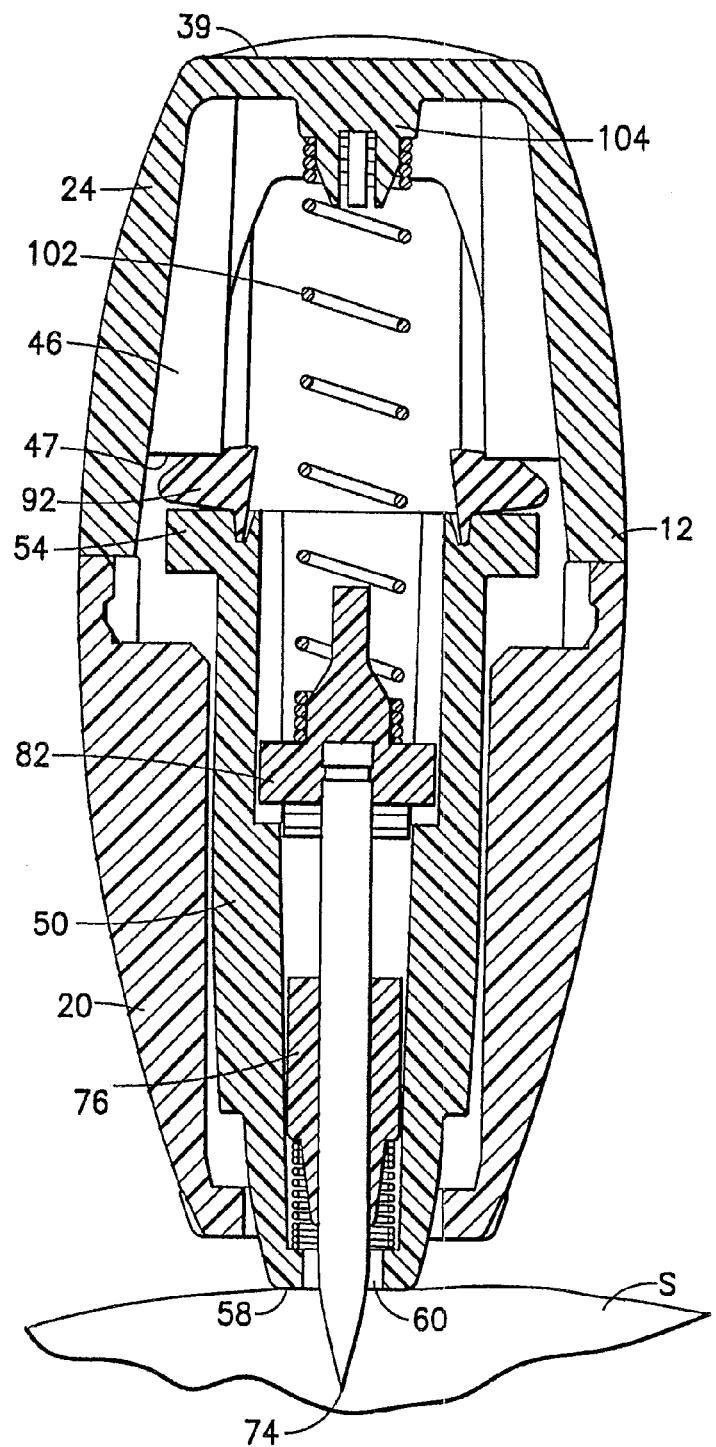
FIG. 17 is a cross-sectional view of the lancet device of FIG. 11D in use with the lancet structure in the puncturing position.
Figure 18:
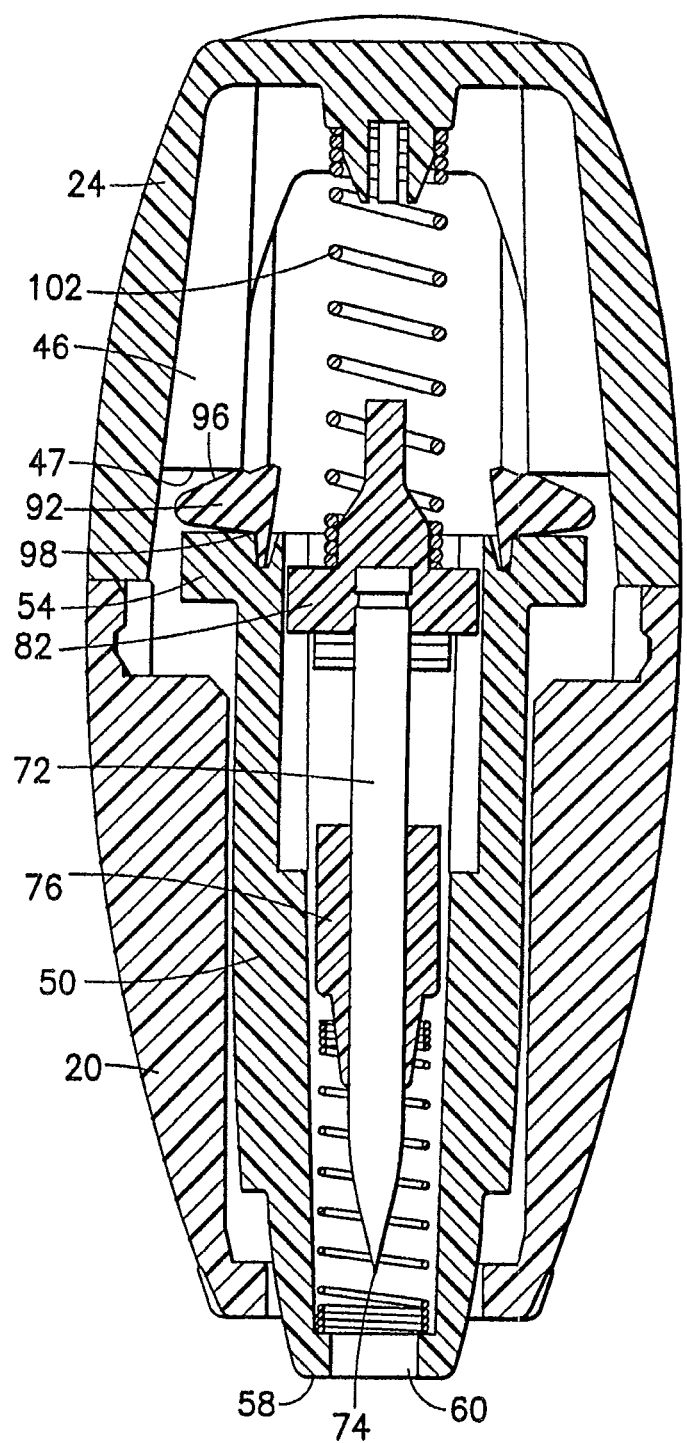
FIG. 18 is a cross-sectional view of the lancet device of FIG. 11D after use with the lancet structure in the final retracted position.

Returning to the actuation as shown in FIG. 17, the biasing force of drive spring 102 propels the lancet structure 70 through shield body 50 to a puncturing position, in which puncturing end 74 of lancet 72 extends through the forward opening 60 through forward end wall 58 a sufficient distance to permit the puncturing end 74 to puncture the skin surface S. The bottom surface 81 of the guide channels 80 within shield body 50 provides an abutment surface for guide tab 78 to prevent the lancet structure 70 from axial movement entirely out of shield body 50 through forward opening 60 during such propelling. Moreover, during such propelling, the forward surface 88 of carrier element 76 contacts the rearward end of retraction spring 110, which is maintained within the forward end 52 of shield body 50, desirably in a relaxed condition in the pre-actuated and/or armed state of the lancet device. The propelling force from the bias of drive spring 102 causes such contact with retraction spring 110, thereby compressing retraction spring 110 between the forward surface 88 of lancet structure 70 and the interior of the forward end wall 58 of shield body 50. The structure of retraction spring 110 is designed such that it is compressible, based upon the biasing force of drive spring 102 propelling lancet structure 70, to permit puncturing end 74 of lancet 72 to extend through forward opening 60. Moreover, the retraction spring 110 is a compression spring, and is therefore capable of being compressed in this manner, but includes sufficient resiliency to return to a relaxed condition after the lancet structure 70 extends to the puncturing position. Accordingly, the biasing force of the compression spring 110 between the forward end wall 58 of the shield body 50 and the lancet structure 70 when in a relaxed state exceeds the biasing force of the drive spring 102 acting between the rear cap 24 of the housing 12 and the rear nub 86 of the lancet structure 70 after the drive spring drives the lancet structure 70 to the puncturing position. In this manner, the retraction spring 110 will relax to an uncompressed state, thus applying a biasing force between the forward surface 88 of the lancet structure 70 and the interior surface of the forward end wall 58, thereby forcing the lancet structure 70 rearward toward the rear cap 24. Such biasing force retracts the puncturing end 74 of lancet 72 within the shield body 50 to a position in which it is shielded from exposure through forward opening 60. Moreover, the opposing forces acting between the drive spring 102 and the retraction spring 110, and the respective forces of such springs based on the structure thereof; maintains the lancet structure 70 disposed within the housing 12 with puncturing end 74 shielded within shield body 50, preventing further movement of lancet structure 70 to the puncturing position.

Moreover, after activation of the lancet device, that is, after the lancet structure 70 is retracted within the housing 12 after the puncturing position, the shield body 60 and the housing 12 may be locked in a fixed relation. In particular, with shield body 50 axially displaced toward the rear cap 24, locking fingers 59 may deflect and lock within respective recesses 29, thereby locking shield body 50 in a rearward position with respect to rear cap 24 and housing 12. The lancet device 10 is therefore safely protected from re-use and may be properly discarded, such as in an appropriate medical waste container.

Figure 20:
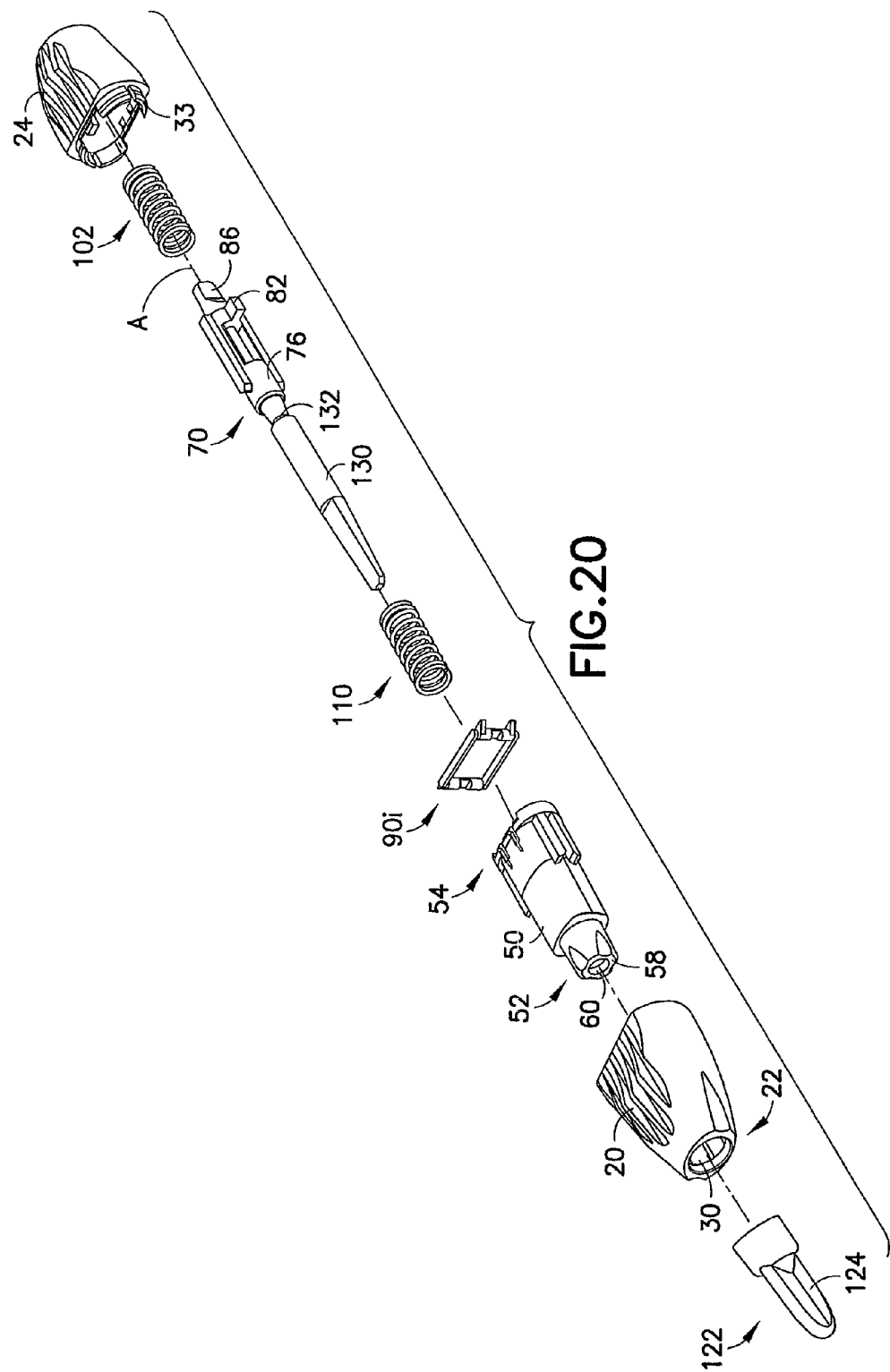
FIG. 20 is a perspective view of a further embodiment of a lancet device of the present invention.
Figure 22:
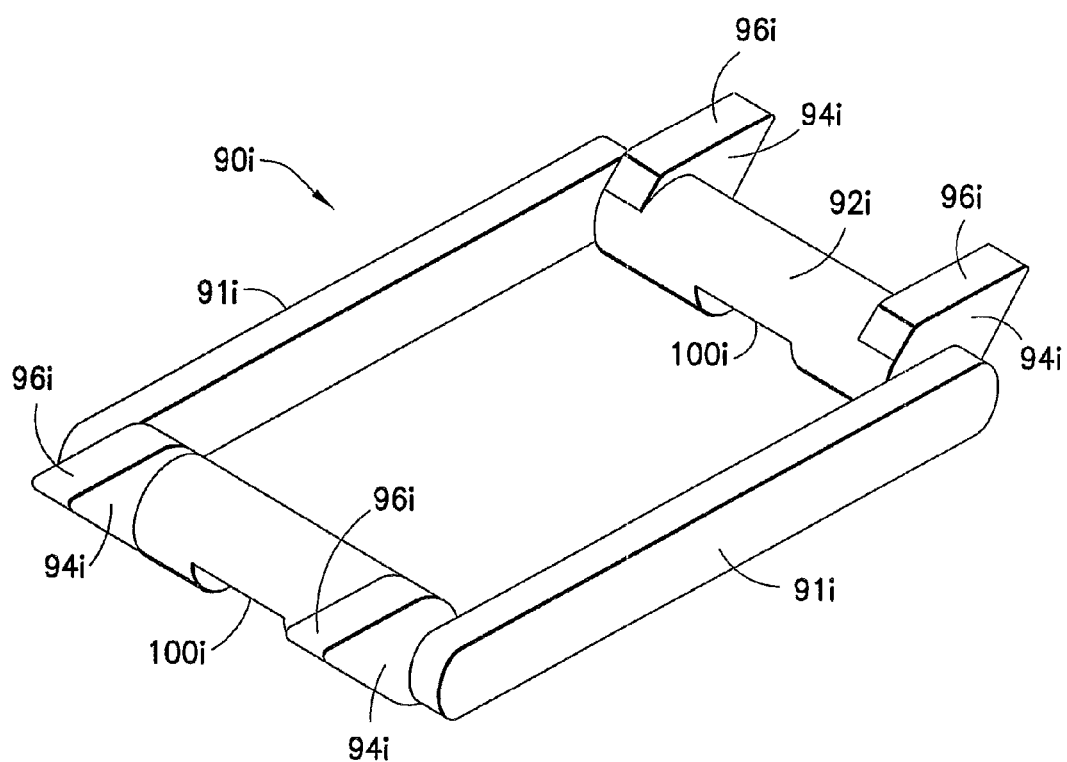
FIG. 22 is a perspective view of the retaining hub shown in FIGS. 21A-21C.

Referring to FIGS. 20-22, the lancet device may include a modified version of a retaining hub 90i. FIG. 20 shows the retaining hub 90i as part of the lancet device 10 as disclosed above, with similar reference numbers shown in FIGS. 20-22 referring to similar elements described in connection with FIGS. 1-18. Retaining hub 90i generally defines an annular shape and is adapted to maintain the lancet structure 70 in an initial armed position retracted within the housing defined by main body 20 and rear cap 24. Retaining hub 90i typically includes two opposed and elongated support members 91i connected by two pivotal cam elements 92i to form the annular shape of retaining hub 90i. Cam elements 92i each include two outward-extending shafts 93i engaged pivotally with the opposed support members 91i. Cam elements 92i each further include at least one typically wedge-shaped contact element 94i defining an upper contact surface 96i on the upper surface thereof. Cam elements 92i each further define a generally centrally located recess or cut-out 100i defined in a bottom side thereof. The purpose of recess 100i is described herein in connection with the operation of retaining hub 90i in lancet device 10. As shown in FIGS. 21A and 22, the cam elements 92i desirably each include two contact elements 94i disposed generally at opposite ends of the cam elements 92i, with the recess 100i defined in the bottom side of the cam elements 92i between the contact elements 94i.

In the lancet device of this embodiment, retaining hub 90i and lancet structure 70 are in interference engagement with each other, such that retaining hub 90i retains the lancet structure 70 in an initial armed state retracted within the housing. For example, fingers 82 on carrier element 76 may rest on the upper side of cam elements 92i, thereby providing interference engagement between the lancet structure 70 and the retaining hub 90i. Moreover, upper contact surface 96i on the contact elements 94i may be adapted for contacting engagement with structure within the housing. For example, rear cap 24 may include structure extending therein, such as internal contact 46 integrally formed and extending on at least one, and desirably on two opposing inner sidewalls thereof. As retaining hub 90i typically includes two contact elements 94i on each cam element 92i, two internal contacts such as contacts 46 described above may be provided on each of the two opposing inner sidewalls of the housing. Each internal contact includes a distal engagement cam surface such as cam surface 47 described above for contacting engagement with the corresponding contact surface 96i on contact elements 94i.

During usual operation of the lancet device of FIGS. 20-22, axial or longitudinal movement of shield body 50 toward rear cap 24, causes the retaining hub 90i to be displaced rearwardly toward rear cap 24, with fingers 82 of the carrier element 76 resting upon the cam elements 92i. Such rearward movement of retaining hub 90i causes the contact surfaces of the engagement cam surfaces of the internal contacts within rear cap 24 to engage and co-act with the corresponding contact surfaces 96i on the contact elements 94i of cam elements 92i. Such engagement and continued downward or distal movement of the internal contacts causes the cam elements 92i to pivot on or rotate about shafts 93i with respect to support members 91i. Due to the generally wedge-shaped profile of the contact elements 94i, the pivotal movement of cam elements 92i has the effect of further compressing drive spring 102 by further "lifting" fingers 82, at least until the point where rear nub 86 on carrier element 76 contacts the inner side of rear cap 24. At this point, continued axial or longitudinal displacement of shield body 50 toward rear cap 24 pivots cam elements 92i to a position where recess 1001 defined in the bottom side of cam elements 92i has rotated to a position generally aligned with fingers 82 at which point the interference engagement between fingers 82 and cam elements 92i is released by such alignment. The biasing force of drive spring 102 then propels lancet structure 70 downward away from the rear cap 24 axially through the housing and through shield body 50 axially through the annular opening defined by retaining hub 90i.

Referring to FIGS. 23A-23D, a further variation or modification of the lancet device is generally illustrated in a further embodiment. In the embodiment of FIGS. 23A-23D, a puncturing device in the form of lancet device 200 is shown. The lancet device 200 generally includes a housing 211, a shield 213 received partially within and axially movable relative to the housing 211, and a skin puncturing assembly 215 (which may be similar to the lancet structure 70 discussed above) disposed within the housing 211. The housing 211 is preferably a generally tubular structure having a distal end 216 and a proximal end 218, and may include similar structure to the housing 12 discussed above in connection with FIGS. 1-18 including a main body 20 and a rear cap 24. Desirably, the housing 211 is open-ended at the distal and proximal ends 216, 218. An end cap 240 may be provided at the proximal end 216 of the housing 211 to close the proximal end 218 of the housing 211. Alternatively, the housing 211 may be formed to have a closed proximal end 218 instead of the end cap 240. In such an embodiment, the closed proximal end 218 of the housing 211 would be integrally formed with the remainder of the body of the housing 211 in this variation of the puncturing device 200. The skin puncturing assembly 215 may further include a protective tip guard 282 connected to a carrier member 250. The tip guard 282 may be formed integrally with the body of the carrier member 250, and may include a notched connection with the carrier member 250 in a similar manner as with protective cover 120 described above.

Flexure members 238 are formed or provided on a proximal end 244 of the shield 213. The flexure members 238 define structure for retaining the lancet structure in an initial armed position retracted within the housing, acting in a similar manner as the pivotal lever element and the retaining hub of the embodiments previously described in connection with FIGS. 1-19. For example, projections 276 on the flexure members 238 extend inward so as to engage or coact with the carrier member 250 of the skin puncturing assembly 215. The projections 276 engage or extend into a circumferential recess 200 defined or formed in the carrier member 250. The recess 210 defines a circumferential edge 212, which is engaged by the projections 276 of the flexure members 238. The engagement edges 277 of the projections 276 in the lancet device 210 illustrated in FIGS. 23A-23D are formed or defined by a radially inward-extending tab 214 on each of the projections 276. Engagement edges 277 act in a similar manner as shoulder 94 described above with reference to FIGS. 1-18, with the load represented by the skin puncturing assembly 215 resting on the engagement edges 277.

The projections 276 maintain the carrier member 250, and thus the skin puncturing assembly 215, in the retracted position until released of engagement with the carrier member 250 by axial displacement of the shield 213 into the housing 211. In the pre-actuated state of the lancet device 200, the biasing force of the drive spring 270 is restrained by the projections 276 and by engagement of the distal end 242 of the shield 213 with an interfering structure provided at the distal end 216 of the housing 211. In particular, while the shield 213 is axially or longitudinally movable or displaceable into the housing 211, the shield 213 is prevented from moving distally relative to the housing 211 by an edge 217 formed on the shield 213. The edge 217 is formed or defined by a portion 219 of the shield 213 having an increased wall thickness. The edge 217 coacts or engages with an internal lip 220 formed at the distal end 216 of the housing 211 to restrain the force of the drive spring 270. The engagement of the edge 217 with the lip 220 allows the flexure members 238 to maintain the carrier member 250 in the retracted position and restrain the force of the drive spring 270. In particular, in the pre-actuated state of the lancet device 200, the force of the drive spring 270 is transmitted via the projections 276 to the body of the shield 213, which causes the edge 217 on the shield 213 to engage the lip 220 and restrain the force of the drive spring 270.

Figure 23A:
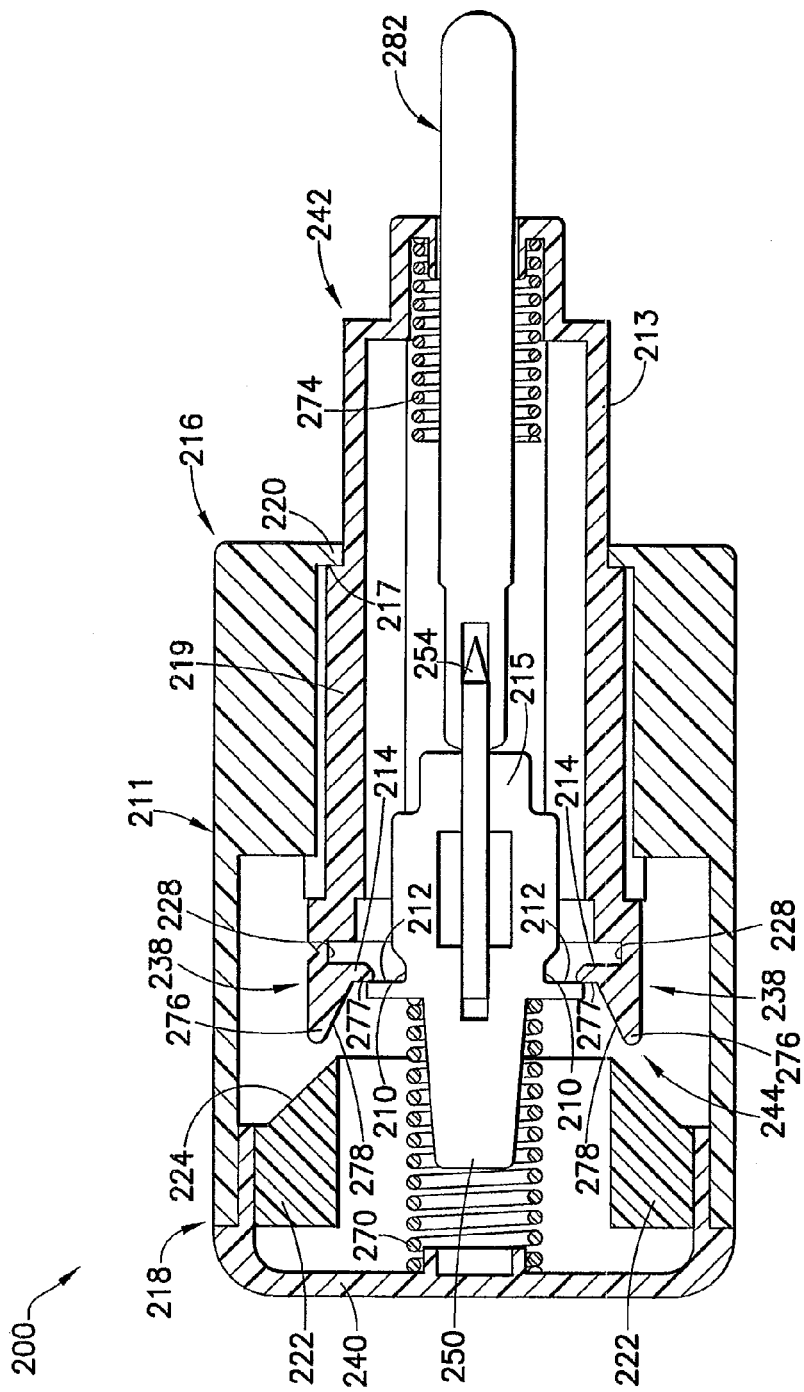
FIGS. 23A-23D are longitudinal cross-sectional views of another embodiment of a medical puncturing device, showing the device prior to actuation and the operational steps for actuating the device.
Figure 23B:
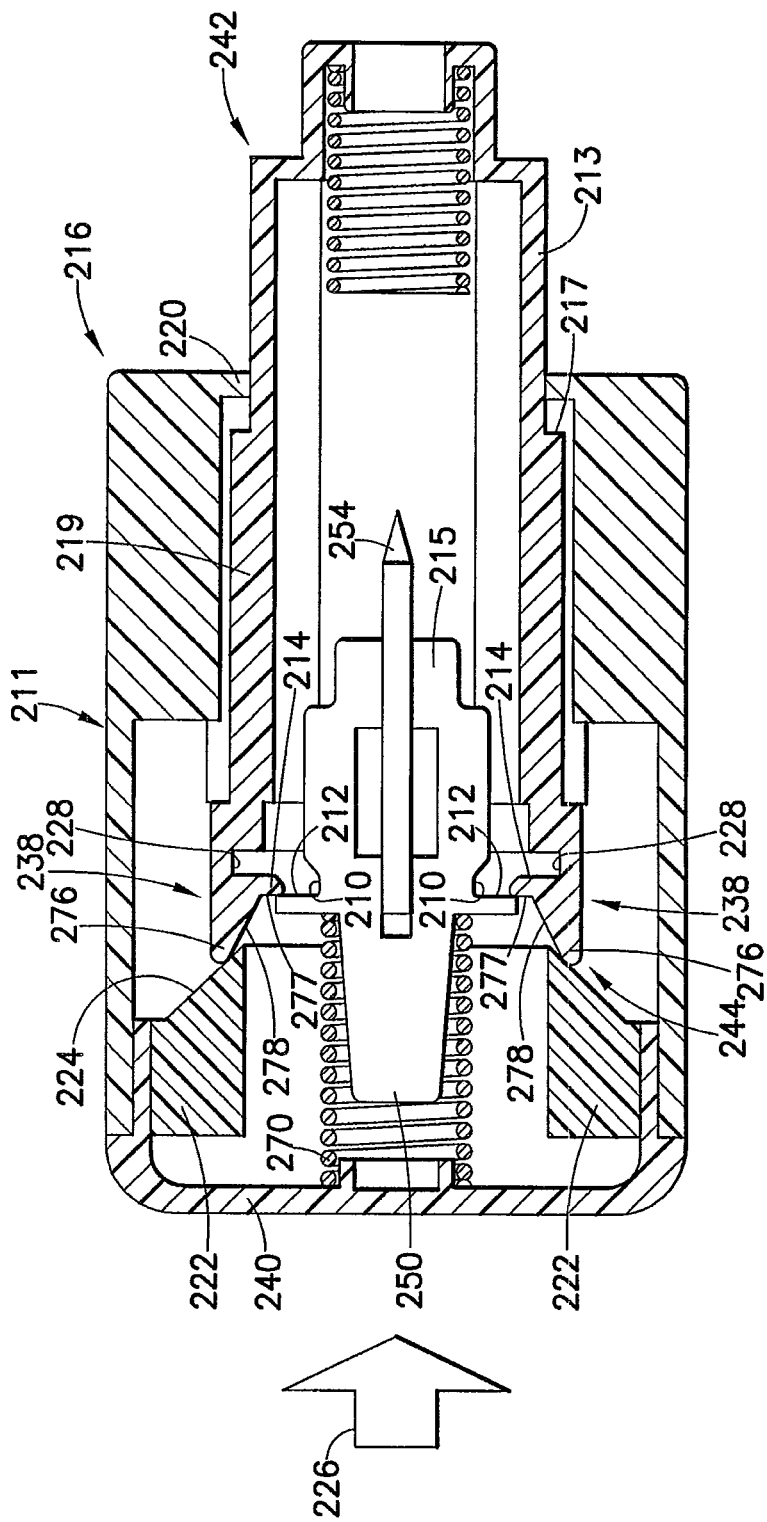
Figure 23C:
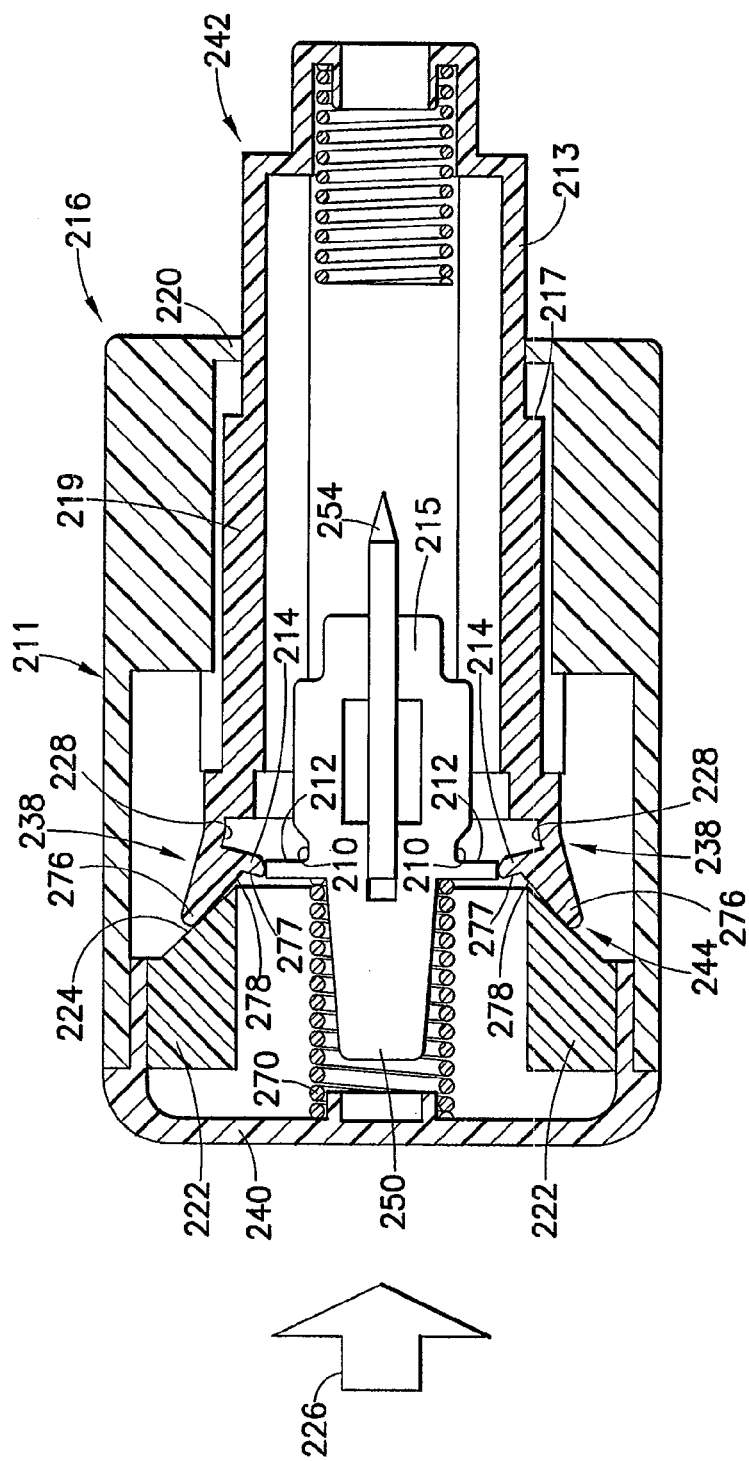
Figure 23D:
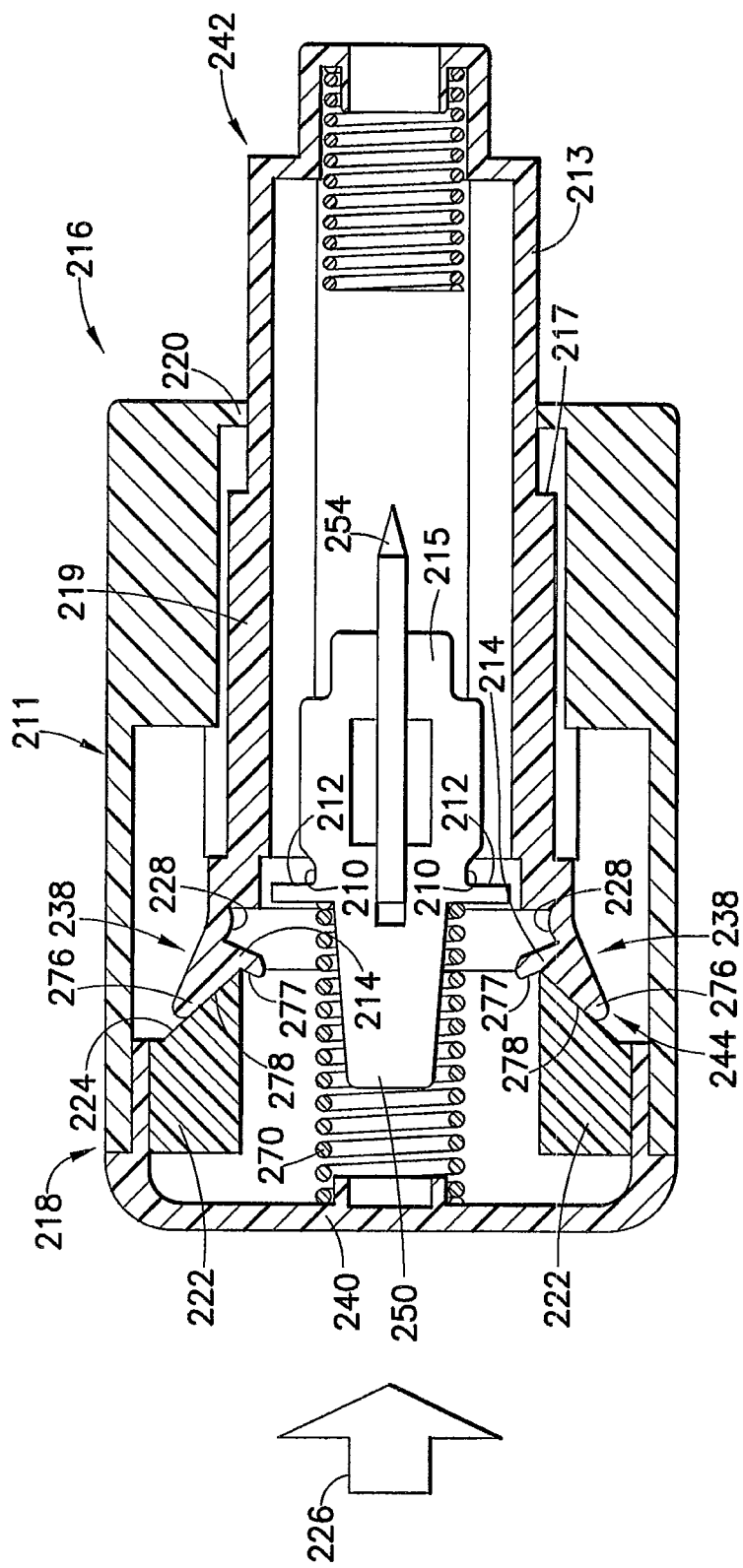

The flexure members 238 are adapted to be released of engagement with the carrier member 250 by one or more actuating members 222 (similar to the internal contact 46 in the embodiment described above with reference to FIGS. 1-18). The actuating member 222 may be formed integrally with the end cap 240, or may be formed separately therefrom and secured to the end cap 240 with, for example, an adhesive. The actuating member 222 includes a tapered camming surface 224 (similar to engagement surface 47), which is adapted to coact or engage with the tapered camming surfaces 278 of the flexure members 238 for actuating the puncturing device 200. In particular, to actuate the puncturing device 200 shown in FIGS. 23A-23D, the user, typically a medical practitioner, places the distal end 242 of the shield 213 in contact with the body part where a blood sample is to be taken, and applies pressure in the direction of arrow 226 in FIGS. 23A-23D to cause the shield 213 to move proximally into the housing 211. The movement of the shield 213 into the housing 211 causes the opposing camming surfaces 278, 224 on the flexure members 238 and actuating member 222, respectively, to engage and interact. As the shield 213 is displaced or moved into the housing 211, the flexure members 238 are flexed radially outward due to the interaction of the opposing camming surfaces 278, 224, as shown in FIGS. 23C and 23D. The flexure members 238 may be adapted or configured to bend or break once they are flexed radially outward a preset distance, angle of rotation, or amount. For example, the flexure members 238 may be formed with a weakened area 228, such as a score line, so that the flexure members 238 break when flexed radially outward a preset distance or degree of rotation. Moreover, weakened area 228 may act as a hinge in a similar manner as pivot hinge 98 described above.

During such movement of the flexure members 238, projections 276 tilt toward the rear end cap 240, thereby "lifting" or moving carrier member 250 toward rear cap 240 and compressing or further compressing drive spring 240. Once the projections 276 on the flexure members 238 are released of engagement with the carrier member 250, the drive spring 270 is free to move the carrier member 250 from the retracted position to the puncturing position. The drive spring 270 preferably has sufficient stored energy to cause the sharp distal tip 254 of the skin puncturing element 215 to pierce the skin of a person or animal once the flexure members 238 are released of engagement with the carrier member 250.

As the carrier member 250 moves distally and reaches the puncturing position wherein the sharp distal tip 254 of the skin puncturing element 215 is fully exposed, a retraction spring 274 is compressed between the carrier member 250 and the distal end 242 of the shield 213 in a similar manner as retraction spring 110 discussed above with reference to FIGS. 1-18. The compression of the retraction spring 274 provides a return or retraction force that acts on the carrier member 250 to move the carrier member 250 in a return, proximal, or retraction direction in the housing 211, which returns or retracts the skin puncturing element 215 and the sharp distal tip 254 thereof fully into the housing 211 and shield 213. The retraction spring 274 thereafter prevents the reemergence of the skin puncturing element 215 from the housing 211 and shield 213.

While specific embodiments of the lancet device have been described, those skilled in the art may make modifications and alterations without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lancet device comprising:
   a housing;
   a lancet structure comprising a puncturing element, the lancet structure disposed within the housing and adapted for movement between a pre-actuated position wherein the puncturing element is retained within the housing and a puncturing position wherein the puncturing element extends through a forward end of the housing;
   a drive spring biasing the lancet structure toward the puncturing position;
   a retaining hub retaining the lancet structure in the pre-actuated position against the bias of the drive spring, the retaining hub comprising a lever pivotal about a fulcrum, the lever comprising a class 1 lever, the lever providing interference engagement with the lancet structure, the lever comprising a first lever element and a second lever element spaced from the first lever element, the first lever element and the second lever element disposed on opposing sides of the lancet structure; and
   an actuator adapted to pivot the lever about the fulcrum, thereby releasing the lever from interference engagement with the lancet structure, permitting the drive spring to drive the lancet structure toward the puncturing position.

2. The lancet device of claim 1, wherein the actuator comprises an actuation element extending through and into the housing, wherein movement of the actuation element with respect to the housing causes the actuation element to pivot the lever about the fulcrum.

3. The lancet device of claim 2, wherein the actuation element extends through a rearward end of the housing and is movable with respect to the housing to cause the actuation element to pivot the lever about the fulcrum.

4. The lancet device of claim 1, wherein the actuator comprises an internal contact integrally formed within the housing, wherein movement of the housing toward the retaining hub causes the internal contact within the housing to pivot the lever about the fulcrum.

5. The lancet device of claim 4, further comprising a shield extending through the forward end of the housing and movable with respect to the housing, with the retaining hub adjacent a rearward end of the shield.

6. The lancet device of claim 5, wherein the lancet structure is retained by the retaining hub at the rearward end of the shield, and wherein movement of the rearward end of the shield toward the rearward end of the housing causes the actuator to pivot the lever of the retaining hub.

7. The lancet device of claim 5, wherein the lancet structure and the shield include corresponding guiding surfaces for guiding the lancet structure through the shield.

8. The lancet device of claim 5, wherein the shield and the housing include corresponding guiding surfaces for guiding the shield through the housing.

9. The lancet device of claim 5, further comprising a retraction spring for retracting the lancet structure within the shield after the drive spring drives the lancet structure through the shield toward the puncturing position.

10. The lancet device of claim 5, further comprising a locking structure extending between the shield and the housing for maintaining the shield in fixed relation to the housing after the drive spring drives the lancet structure through the shield toward the puncturing position.

11. The lancet device of claim 1, wherein the lever comprises a shoulder in interference engagement with the lancet structure and a contact surface for engagement with an internal contact of the housing.

12. The lancet device of claim 11, wherein the lever comprises a wedge pivotally hinged to the retaining hub forming a pivot hinge defining the fulcrum for cooperative pivoting of the shoulder and the contact surface.

13. The lancet device of claim 12, wherein the retaining hub comprises an annular rim with the lever pivotally hinged to the annular rim.

14. The lancet device of claim 11, wherein the lancet structure further comprises a carrier element including a finger in interference engagement with the shoulder of the lever.

15. A lancet device comprising:
   a housing having a rearward end and a forward end having an opening extending therethrough;
   a shield movable through the opening of the forward end of the housing, the shield comprising a retaining hub adjacent a rearward end thereof, the retaining hub comprising a pivotal lever pivotal about a fulcrum, the lever comprising a class 1 lever;
   a lancet structure comprising a puncturing element, the lancet structure disposed within the housing and adapted for movement between a pre-actuation position wherein the puncturing element is disposed within the housing and a puncturing position, wherein the puncturing element extends through a forward end of the shield, and the lancet structure is in interference engagement with the lever of the retaining hub at the rearward end of the shield thereby maintaining the lancet structure in the retracted position; and
   a drive spring disposed between the housing and the lancet structure for biasing the lancet structure against the lever of the retaining hub,
   wherein movement of the shield toward the rearward end of the housing causes an internal contact within the housing to engage the lever of the retaining hub, thereby causing pivotal movement of the lever to release the lancet structure from interference engagement with the lever, permitting the drive spring to drive the lancet structure through the shield toward the puncturing position.

16. The lancet device of claim 15, wherein the retaining hub comprises an annular rim separate from and retained at the rearward end of the shield.

17. The lancet device of claim 15, wherein the retaining hub comprises an annular rim with the lever pivotally supported on the annular rim.

18. The lancet device of claim 17, wherein the annular rim comprises a pair of levers pivotally supported on opposing sides of the annular rim.

19. The lancet device of claim 15, wherein the lever comprises a shoulder in interference engagement with the lancet structure and a contact surface, such that engagement of the internal contact of the housing with the contact surface of the lever causes the lever to pivot, thereby releasing the lancet structure from interference engagement with the shoulder.

20. The lancet device of claim 19, wherein the internal contact of the housing comprises an integrally formed cam surface for cooperative engagement with the contact surface of the lever.

21. The lancet device of claim 19, wherein the lever comprises a wedge pivotally hinged to the retaining hub forming a pivot hinge for cooperative pivoting of the shoulder and the contact surface.

22. The lancet device of claim 21, wherein the retaining hub comprises an annular rim with the lever pivotally hinged to the annular rim.

23. The lancet device of claim 19, wherein the lancet structure further comprises a carrier element including a finger in interference engagement with the shoulder of the lever.

24. The lancet device of claim 15, wherein the lancet structure and the shield include corresponding guiding surfaces for guiding the lancet structure through the shield.

25. The lancet device of claim 24, wherein the lancet structure includes at least one guide tab on an external surface thereof and the shield includes at least one corresponding guide channel on an internal channel thereof for guiding movement of the lancet structure within the shield.

26. The lancet device of claim 15, wherein the shield and the housing include corresponding guiding surfaces for guiding the shield through the housing.

27. The lancet device of claim 26, wherein the shield includes at least one guide channel on an external surface thereof and the housing includes at least one corresponding guide tab therein for guiding movement of the shield within the housing.

28. The lancet device of claim 15, further comprising a retraction spring for retracting the lancet structure within the shield after the drive spring drives the lancet structure through the shield toward the puncturing position.

29. The lancet device of claim 28, wherein the retraction spring comprises a compression spring positioned within the forward end of the shield for compression between the lancet structure and the forward end of the shield, wherein the biasing force of the compression spring between the forward end of the shield and the lancet structure exceeds the biasing force of the drive spring between the rearward end of the housing and the lancet structure after the drive spring drives the lancet device to the puncturing position, thereby maintaining the puncturing element within the shield.

30. The lancet device of claim 15, further comprising a locking structure extending between the shield and the housing for maintaining the shield in fixed relation to the housing after the drive spring drives the lancet structure through the shield toward the puncturing position.

31. The lancet device of claim 30, wherein the locking structure comprises a frictional engagement between the shield and the housing.

32. The lancet device of claim 30, wherein the shield includes at least one locking finger adjacent the rearward end thereof for locking within a corresponding recess within the housing.

33. The lancet device of claim 15, wherein the housing comprises a main housing element and a rearward cap element.

34. The lancet device of claim 33, wherein the internal contact comprises a cam surface integrally formed within the rearward cap element.

35. The lancet device of claim 15, further comprising a lancet cover removably covering the puncturing element of the lancet structure and extending through the forward end of the shield.

36. The lancet device of claim 35, wherein the lancet cover comprises a post portion substantially enclosing the puncturing element and a forward tab adapted to be grasped by a user.

37. The lancet device of claim 15, wherein the puncturing element includes an alignment orientation, and at least one of the housing or the shield includes target indicia corresponding to the alignment orientation of the puncturing element.

38. A lancet device comprising a housing and a lancet including a puncturing element movable within the housing and retained within the housing against a bias of a drive spring biasing the lancet toward a puncturing position wherein the puncturing element extends through a forward end of the housing, comprising an annular retaining hub comprising a lever in interference engagement with the lancet for retaining the lancet within the housing against the bias of the drive spring, the lever comprising a class 1 lever, the lever being pivotal about a fulcrum on one side of a plane dissecting the annular retaining hub at a cross-section to an axis defined by the lancet, the lever comprising a first lever element and a second lever element spaced from the first lever element, the first lever element and the second lever element disposed on opposite sides of the lancet, wherein pivoting of the lever about the fulcrum upon engagement of the lever with a portion of the housing releases the lancet from interference engagement with the lever to permit the drive spring to drive the lancet toward the puncturing position.

39. The lancet device of claim 38, wherein movement of the housing and the annular retaining hub with respect to each other causes an internal contact within the housing to pivot the lever about the fulcrum.

40. The lancet device of claim 39, further comprising a shield extending through a forward end of the housing and moveable with respect to the housing, the annular retaining hub adjacent a rearward end of the shield, at least a portion of the lancet being moveable through the shield and the annular retaining hub upon release of the lancet from interference engagement with the lever.

41. The lancet device of claim 38, further comprising an actuator having an actuation element extending through and into the housing, wherein movement of the actuation element with respect to the housing causes the actuation element to pivot the lever about the fulcrum.

42. The lancet device of claim 41, wherein the actuation element extends through a rearward end of the housing and is movable with respect to the housing to cause the actuation element to pivot the lever about the fulcrum.

43. A lancet device comprising:
a housing;
a lancet comprising a puncturing element axially movable within the housing and retained within the housing, the lancet movable toward a puncturing position wherein the puncturing element extends through a forward end of the housing;

a drive spring biasing the lancet toward the puncturing position;

a shield extending through the forward end of the housing and moveable with respect to the housing; and an annular retaining hub comprising at least one class 1-type lever being pivotal about a fulcrum, the lever having a first position with respect to the fulcrum wherein the hub restricts movement of the lancet with respect to the shield, and a second position with respect to the fulcrum wherein the hub does not restrict movement of the lancet with respect to the shield, the second position enabling the lancet to achieve a puncture position through the forward end of the shield, wherein movement of the shield with respect to the housing causes movement of the lever from the first position to the second position, thereby releasing the lancet from interference engagement with the lever, and wherein the drive spring has one end engaged to either the shield or the housing and the other end engaged to the lancet, wherein sufficient pivotal movement of the at least one class 1-type lever permits the drive spring to drive the lancet toward the puncturing position.

44. A lancet device comprising:

a housing;

a lancet structure comprising a puncturing element, the lancet structure disposed within the housing and adapted for movement between a pre-actuated position and a puncturing position wherein the puncturing element extends through an end of the housing;

a drive spring for biasing the lancet structure toward the puncturing position;

a retaining hub retaining the lancet structure in the pre-actuated position against the bias of the drive spring, the retaining hub comprising a lever pivotal about a fulcrum, the lever comprising a class 1 lever, the lever providing interference engagement with the lancet structure, the lever comprising a first lever element and a second lever element spaced from the first lever element, the first lever element and the second lever element disposed on opposing sides of the lancet structure; and an actuator adapted to pivot the lever upon engagement of the lever with a portion of the housing thereby releasing the lever from interference engagement with the lancet structure, permitting the drive spring to drive the lancet structure toward the puncturing position.

45. The lancet device of claim 44, wherein the actuator comprises an actuation element extending through and into the housing, wherein movement of the actuation element with respect to the housing causes the actuation element to pivot the lever.

46. The lancet device of claim 44, further comprising a shield extending through the forward end of the housing and movable with respect to the housing, with the retaining hub adjacent a rearward end of the shield and wherein the lancet structure is retained by the retaining hub at the rearward end of the shield such that movement of the rearward end of the shield toward the rearward end of the housing causes the actuator to pivot the lever of the retaining hub.

47. The lancet device of claim 44, wherein the lever comprises a shoulder in interference engagement with the lancet structure and a contact surface for engagement with the internal contact of the housing.

48. The lancet device of claim 47, wherein the lever comprises a wedge pivotally hinged to the retaining hub forming a pivot hinge defining a fulcrum for cooperative pivoting of the shoulder and the contact surface.

49. A lancet device comprising:

a housing having a rearward end and a forward end having an opening extending therethrough;

a shield movable through the opening of the forward end of the housing, the shield comprising a retaining hub adjacent a rearward end thereof, the retaining hub comprising a pivotal lever pivotal about a fulcrum, the lever comprising a class 1 lever;

a lancet structure comprising a puncturing element, the lancet structure disposed within the housing and adapted for movement between a pre-actuation position wherein the puncturing element is disposed within the housing and a puncturing position wherein the puncturing element extends through a forward end of the shield, and the lancet structure is in interference engagement with the lever of the retaining hub thereby maintaining the lancet structure in the retracted position; and a biasing member in cooperation with the lancet structure for biasing the lancet structure against the lever of the retaining hub, wherein movement of the shield causes pivotal movement of the lever upon engagement of the lever with a portion of the housing to release the lancet structure from interference engagement with the lever, permitting the biasing member to drive the lancet structure through the shield toward the puncturing position.

50. The lancet device of claim 49, wherein the retaining hub comprises an annular rim separate from and retained at the rearward end of the shield and includes a pair of levers pivotally supported on opposing sides of the annular rim.

51. The lancet device of claim 49, wherein the lancet structure further comprises a carrier element including a finger in interference engagement with a shoulder of the lever.

52. The lancet device of claim 49, wherein the lancet structure and the shield include corresponding guiding surfaces for guiding the lancet structure through the shield.

53. The lancet device of claim 49, wherein the shield and the housing include corresponding guiding surfaces for guiding the shield through the housing.

54. The lancet device of claim 49, further comprising a retraction spring and wherein the retraction spring comprises a compression spring positioned within the forward end of the shield for compression between the lancet structure and the forward end of the shield, wherein the biasing force of the compression spring between the forward end of the shield and the lancet structure exceeds the biasing force of the biasing member between the rearward end of the housing and the lancet structure after the biasing member drives the lancet device to the puncturing position, thereby maintaining the puncturing element within the shield.

55. The lancet device of claim 49, wherein the shield includes at least one locking finger adjacent the rearward end thereof for locking within a corresponding recess within the housing for maintaining the shield in fixed relation to the housing after the biasing member drives the lancet structure through the shield toward the puncturing position.

56. The lancet device of claim 49, wherein the housing comprises a main housing element and a rearward cap element and wherein the internal contact comprises a cam surface integrally formed within the rearward cap element.

57. The lancet device of claim 49, further comprising a lancet cover removably covering the puncturing element of the lancet structure and extending through the forward end of the shield.

58. The lancet device of claim 49, wherein the puncturing element includes an alignment orientation, and at least one of the housing or the shield includes target indicia corresponding to the alignment orientation of the puncturing element.

59. A lancet device comprising:
- a housing;
- a lancet comprising a puncturing element axially movable within the housing and retained within the housing, the lancet movable toward a puncturing position wherein the puncturing element extends through a forward end of the housing;
- a shield extending through the forward end of the housing and moveable with respect to the housing; and
- an annular retaining hub comprising a lever pivotal about a pivot point upon engagement of the lever with a portion of the housing, the lever comprising a class 1 lever, the lever having a first position with respect to the pivot point wherein the hub restricts movement of the lancet with respect to the shield, and a second position with respect to the pivot point wherein the hub does not restrict movement of the lancet with respect to the shield, the second position enabling the lancet to achieve a puncture position through the forward end of the shield, the lever comprising a first lever element and a second lever element spaced from the first lever element, the first lever element and the second lever element disposed on opposing sides of the lancet,
- wherein movement of the shield with respect to the housing causes movement of the lever from the first position to the second position, thereby releasing the lancet from interference engagement with the lever.

60. The lancet device of claim 59, comprising a biasing member having one end engaged to either the shield or the housing and the other end engaged to the lancet, wherein sufficient pivotal movement of the lever permits the biasing member to drive the lancet toward the puncturing position.

* * * * *